United States Patent
Liphardt

(10) Patent No.: US 7,518,725 B1
(45) Date of Patent: Apr. 14, 2009

(54) TEMPERATURE CONTROLLED LENS

(75) Inventor: Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 431 days.

(21) Appl. No.: 11/585,301

(22) Filed: Oct. 23, 2006

Related U.S. Application Data

(63) Continuation-in-part of application No. 11/103,229, filed on Apr. 12, 2005, and a continuation-in-part of application No. 10/829,620, filed on Apr. 22, 2004, now Pat. No. 7,193,710, and a continuation-in-part of application No. 10/034,800, filed on Dec. 28, 2001, now Pat. No. 6,822,738, and a continuation-in-part of application No. 09/583,229, filed on May 30, 2000, now Pat. No. 6,804,004, and a continuation-in-part of application No. 09/419,794, filed on Oct. 18, 1999, and a continuation-in-part of application No. 09/162,217, filed on Sep. 29, 1998, now Pat. No. 6,034,777, and a continuation-in-part of application No. 09/144,764, filed on Aug. 31, 1998, now Pat. No. 5,969,818, and a continuation-in-part of application No. 09/033,694, filed on Mar. 3, 1998, now Pat. No. 5,963,327, said application No. 11/585,301 and a continuation-in-part of application No. 10/699,540, filed on Nov. 1, 2003, now Pat. No. 7,158,231, and a continuation-in-part of application No. 09/945,962, filed on Sep. 4, 2001, and a continuation-in-part of application No. 09/517,125, filed on Feb. 29, 2000, and a continuation-in-part of application No. 09/246,888, filed on Feb. 8, 1999, now Pat. No. 6,084,675, is a continuation-in-part of application No. 08/912,211, filed on Aug. 15, 1997, now Pat. No. 5,872,630, and a continuation-in-part of application No. 08/618,820, filed on Mar. 20, 1996, now Pat. No. 5,706,212, and a continuation-in-part of application No. 08/530,892, filed on Sep. 20, 1995, now Pat. No. 5,666,201, said application No. 11/585,301 and a continuation-in-part of application No. 09/232,257, filed on Jan. 19, 1999, now Pat. No. 6,141,102, and a continuation-in-part of application No. 09/225,118, filed on Jan. 4, 1999, now Pat. No. 6,084,674, and a continuation-in-part of application No. 09/223,822, filed on Jan. 4, 1999, now Pat. No. 6,118,537, and a continuation-in-part of application No. 09/225,371, filed on Jan. 4, 1999, now Pat. No. 6,100,981, and a continuation-in-part of application No. 09/225,076, filed on Jan. 4, 1999, now Pat. No. 5,963,325.

(60) Provisional application No. 60/527,554, filed on Dec. 6, 2003, provisional application No. 60/527,638, filed on Dec. 8, 2003, provisional application No. 60/733,599, filed on Nov. 7, 2005, provisional application No. 60/094,104, filed on Jul. 24, 1998.

(51) Int. Cl.
*G01J 4/00* (2006.01)
*G02B 21/26* (2006.01)

(52) U.S. Cl. .................... 356/369; 356/364; 359/362; 359/395

(58) Field of Classification Search ......... 356/364–369; 359/362, 371, 395
See application file for complete search history.

(56) References Cited

U.S. PATENT DOCUMENTS 2,700,918 A   2/1955 Osterberg et al.
(Continued)

FOREIGN PATENT DOCUMENTS

EP   1 172 642 A2   1/2002
(Continued)

OTHER PUBLICATIONS

Japanese App. H6 (1994)—22332, Aug. 1995.
(Continued)

*Primary Examiner*—L. G Lauchman
(74) *Attorney, Agent, or Firm*—James D. Welch

(57) ABSTRACT

Quasi-achromatic multi-element lens(es), the elements of which are mounted with respect to one another in a temperature controlled mounting system, and the application thereof in focusing, (and/or colliminating), a spectroscopic electromagnetic beam into a very small, chromatically relatively undispersed, area spot on a material system, and application thereof in ellipsometer, polarimeter and the like systems.

41 Claims, 6 Drawing Sheets

U.S. PATENT DOCUMENTS

| | | | | |
|---|---|---|---|---|
| 3,183,763 | A | 5/1965 | Koester | |
| 3,992,104 | A | 11/1976 | Watanabe | 356/117 |
| 4,053,232 | A | 10/1977 | Dill et al. | 356/118 |
| 4,105,338 | A | 8/1978 | Kuroha | 356/118 |
| 4,210,401 | A | 7/1980 | Batten | 356/369 |
| 4,332,476 | A | 6/1982 | Stenberg et al. | 356/369 |
| 4,355,903 | A | 10/1982 | Sandercock | 356/382 |
| 4,373,817 | A | 2/1983 | Coates | 356/384 |
| 4,556,292 | A | 12/1985 | Mathyssek et al. | 350/394 |
| 4,636,075 | A | 1/1987 | Knollenberg | 356/336 |
| 4,647,207 | A | 3/1987 | Bjork et al. | 356/369 |
| 4,668,860 | A | 5/1987 | Anthon | 250/225 |
| 4,671,657 | A | 6/1987 | Calvani et al. | 356/484 |
| 4,750,822 | A | 6/1988 | Rosencwaig et al. | 356/445 |
| 4,826,321 | A | 5/1989 | Coates et al. | 356/351 |
| 4,838,695 | A | 6/1989 | Mansuripur et al. | 356/369 |
| 4,893,932 | A | 1/1990 | Knollenberg | 356/369 |
| 5,042,957 | A | 8/1991 | Gold et al. | 356/369 |
| 5,045,704 | A | 9/1991 | Coates | 356/448 |
| 5,166,752 | A | 11/1992 | Spanier et al. | 356/369 |
| 5,329,357 | A | 7/1994 | Bernoux et al. | 356/369 |
| 5,349,471 | A | 9/1994 | Morris | 359/565 |
| RE34,783 | E | 11/1994 | Coates | 250/372 |
| 5,373,359 | A | 12/1994 | Woollam et al. | 356/328 |
| 5,475,525 | A | 12/1995 | Tournois et al. | 359/245 |
| 5,504,582 | A | 4/1996 | Johs et al. | 356/369 |
| 5,521,706 | A | 5/1996 | Green et al. | 356/369 |
| 5,581,350 | A | 12/1996 | Chen et al. | 356/369 |
| 5,596,411 | A | 1/1997 | Fanton et al. | 356/369 |
| 5,608,526 | A | 3/1997 | Piwonka-Corle et al. | 356/369 |
| 5,666,201 | A | 9/1997 | Johs et al. | 356/369 |
| 5,706,212 | A | 1/1998 | Thompson et al. | 364/525 |
| 5,757,494 | A | 5/1998 | Green et al. | 356/369 |
| 5,872,630 | A | 2/1999 | Johs et al. | 356/369 |
| 5,877,859 | A | 3/1999 | Aspnes | 356/364 |
| 5,917,594 | A | 6/1999 | Norton | 356/327 |
| 5,946,098 | A | 8/1999 | Johs et al. | 356/364 |
| 5,956,145 | A | 9/1999 | Green et al. | 356/364 |
| 5,963,325 | A | 10/1999 | Johs et al. | 356/364 |
| 5,963,327 | A | 10/1999 | He et al. | 356/369 |
| 5,978,087 | A | 11/1999 | Patterson et al. | 356/369 |
| 6,084,674 | A | 7/2000 | Johs et al. | 356/364 |
| 6,084,675 | A | 7/2000 | Herzinger et al. | 356/369 |
| 6,100,981 | A | 8/2000 | Johs et al. | 356/364 |
| 6,118,537 | A | 9/2000 | Johs et al. | 356/369 |
| 6,141,102 | A | 10/2000 | Johs et al. | 356/364 |
| 6,268,917 | B1 | 7/2001 | Johs | 356/369 |
| 6,804,004 | B1 * | 10/2004 | Johs et al. | 356/369 |
| 7,215,424 | B1 * | 5/2007 | Liphardt et al. | 356/369 |
| 7,336,361 | B1 * | 2/2008 | Liphardt et al. | 356/369 |
| 2002/0024669 | A1 | 2/2002 | Danner et al. | |

FOREIGN PATENT DOCUMENTS

| | | |
|---|---|---|
| JP | 2002 2098591 A | 4/2002 |
| WO | WO 92/12404 | 7/1992 |
| WO | WO 96/18205 | 6/1996 |
| WO | WO 99/02950 | 1/1999 |
| WO | WO 91/14157 | 3/2000 |

OTHER PUBLICATIONS

Paper by Johs, titled "Regression Calibration Method for Rotating Element Ellipsometers", Thin Solid Films, 234 (1993).

Paper, by Gottesfeld et al., titled "Combined Ellipsometer and Reflectometer Measurements of Surface Processes on Nobel Metals Electrodes", Surface Sci., 56 (1976).

Paper by Smith, titled "An Automated Scanning Ellipsometer", Surface Science, vol. 56, No. 1. (1976).

Papers, by Azzam and Azzam et al. are also identified as concerning alternative approaches to the goal of the present invention, and are titled: "Multichannel Polarization State Detectors For Time-Resolved Ellipsometry", Thin Solid Film, 234 (1993); and "Spectrophotopolarimeter Based On Multiple Reflections In A Coated Dielectric Slab", Thin Solid Films 313 (1998); and "General Analysis and Optimization Of The Four-Detector Photopolarimeter", J. Opt. Soc. Am., A, vol. 5, No. 5 (May 1988); and "Accurate Calibration Of Four-Detector Photopolarimeter With Imperfect Polarization Optical Elements", J. Opt. Soc. Am., vol. 6, No. 10, (Oct. 1989).

Review paper by Collins, titled "Automatic Rotating Element Ellipsometers: Calibration, Operation and Real-Time Applications", Rev. Sci. Instrum., 61(8) (1990), is identified for general information.

* cited by examiner

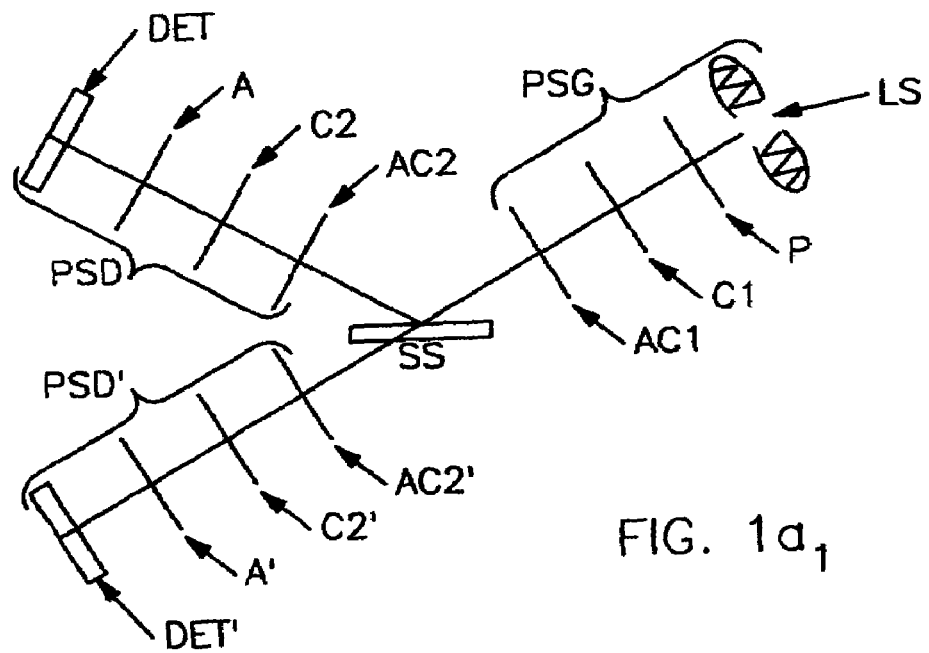
FIG. $1a_1$
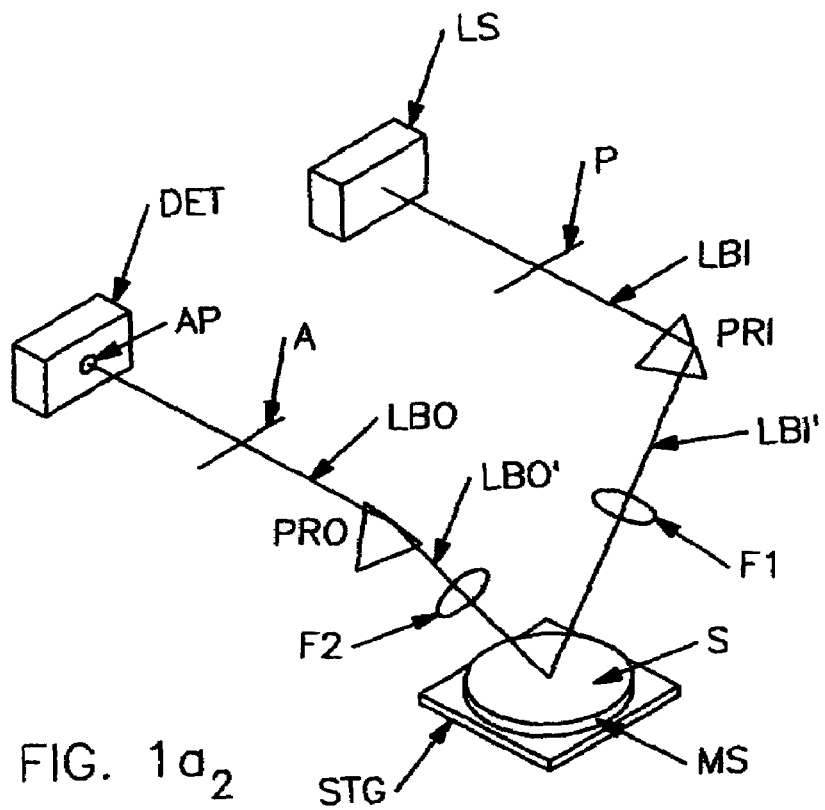
FIG. $1a_2$

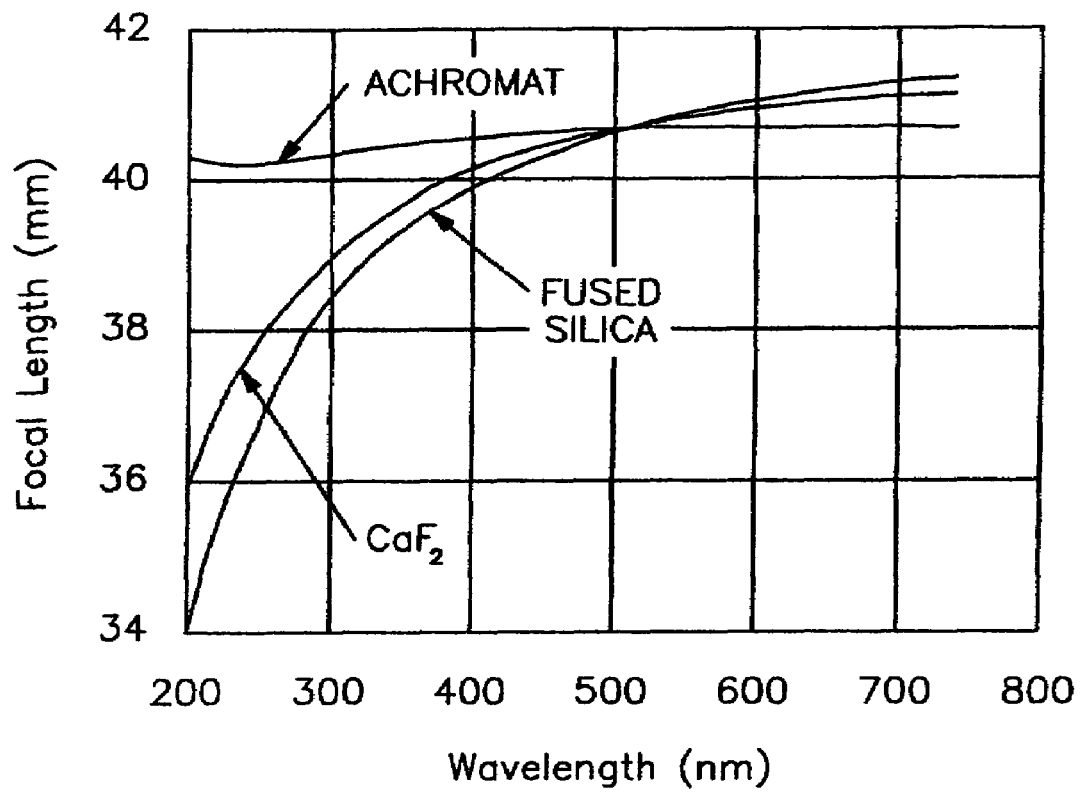
FIG. 1a₆
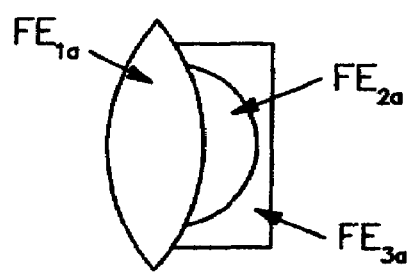
FIG. 1a₃

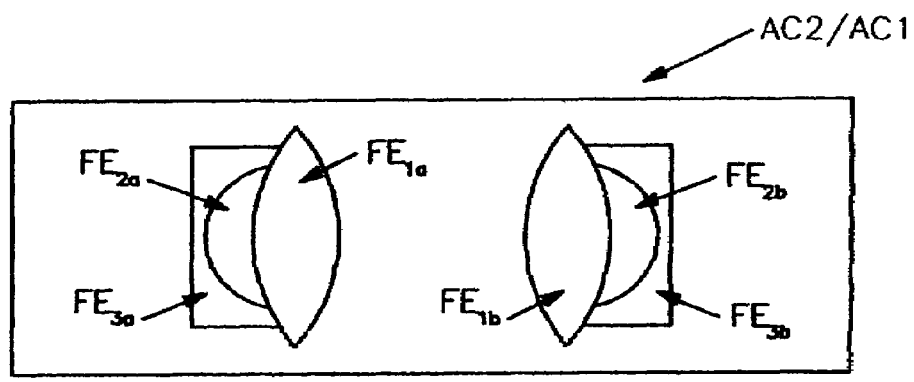
FIG. $1a_4$
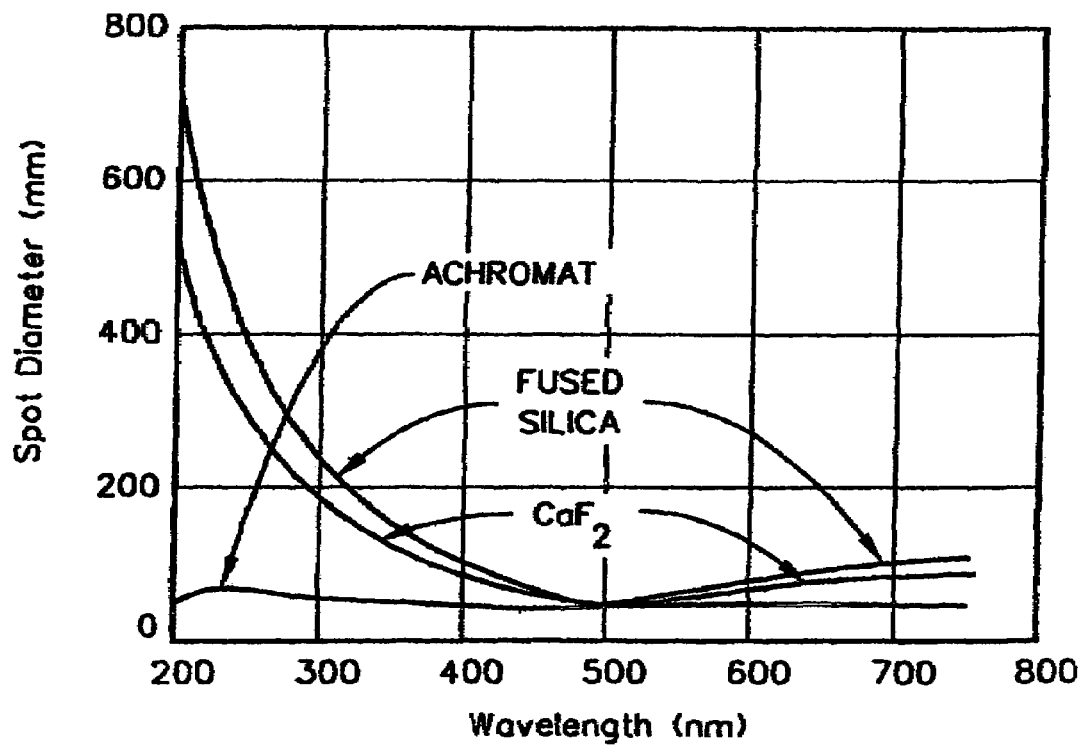
FIG. $1a_5$

FIG. 1a$_7$
FIG. 1a$_8$
FIG. 1a$_9$
FIG. 1a$_{10}$
FIG. 1a$_{11}$
FIG. 1a$_{12}$
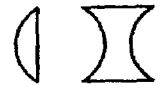
FIG. 1a$_{13}$
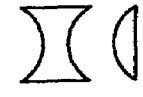
FIG. 1a$_{14}$
FIG. 1a$_{15}$
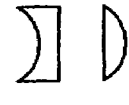
FIG. 1a$_{16}$
FIG. 1a$_{17}$
FIG. 1a$_{18}$
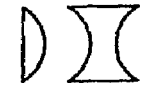
FIG. 1a$_{19}$
FIG. 1a$_{20}$
FIG. 1a$_{21}$
FIG. 1a$_{22}$
FIG. 1a$_{23}$
FIG. 1a$_{24}$
C D C D
FIG. 1a$_{25}$
C D D C
FIG. 1a$_{26}$
D C D C
FIG. 1a$_{27}$
D C C D
FIG. 1a$_{28}$

TEMPERATURE CONTROLLED LENS

This application Claims Benefit of Provisional Application Ser. No. 60/733,599, Filed Nov. 7, 2005.

This application is a CIP of Co-pending application Ser. No. 11/103,229 Filed Apr. 12, 2005. This application is also a Continuation-in-Part of application Ser. No. 10/829,620 Filed Apr. 22, 2004, now U.S. Pat. No. 7,193,710 and therevia of No. 10/034,800 Filed Dec. 28, 2001 now U.S. Pat. No. 6,822,738 and of application Ser. No. 09/583,229 Filed May 30, 2000 and therevia of 09/162,217 Filed Sep. 29, 1998 (now U.S. Pat. No. 6,034,777), of 09/033,694 Filed Mar. 3, 1998 (now U.S. Pat. No. 5,963,327); of 09/144,764 Filed Aug. 31, 1998 (now U.S. Pat. No. 5,969,818), of 09/419,794 Filed Oct. 18, 1999, and of 09/144,764 Filed Aug. 31, 1998 and therevia Claims benefit of Provisional 60/094,104 Filed Jul. 24, 1998.

This application further is a Continuation-in-Part of application Ser. No. 10/699,540 Filed Nov. 1, 2003 now U.S. Pat. No. 7,158,231 and therevia of Copending application Ser. No. 09/945,962 Filed Sep. 4, 2001, application Ser. No. 09/517,125 Filed Feb. 29, 2000, and therevia of application Ser. No. 09/246,888 filed Feb. 8, 1999, (now U.S. Pat. No. 6,084,675). Further, via the 09/246,888 application, this application is a Continuation-In-Part of application Ser. No. 08/912,211 filed Aug. 15, 1997, (now U.S. Pat. No. 5,872,630), which was a CIP from application Ser. No. 08/530,892 filed Sep. 20, 1995, (now U.S. Pat. No. 5,666,201); and is a CIP of application Ser. No. 08/618,820 filed Mar. 20, 1996, (now U.S. Pat. No. 5,706,212). This application is further a CIP of application Ser. Nos. 09/225,118 filed Jan. 4, 1999, (now U.S. Pat. No. 6,084,674); 09/223,822 filed Jan. 4, 1999, (now U.S. Pat. No. 6,118,537); 09/232,257 filed Jan. 19, 1999, (now U.S. Pat. No. 6,141,102); 09/225,371 filed Jan. 4, 1999, (now U.S. Pat. No. 6,100,981); Ser. No. 09/225,076 filed Jan. 4, 1999, (now U.S. Pat. No. 5,963,325), which applications depend from application Ser. No. 08/997,311 filed Dec. 23, 1997, (now U.S. Pat. No. 5,946,098).

This application also Claims benefit of Provisional Application Ser. No. 60/527,554, Filed Dec. 6, 2003; and 60/527,638 Filed Dec. 8, 2003.

TECHNICAL FIELD

The present invention relates to ellipsometry and polarimetry, and more particularly comprises quasi-achromatic multi-element lens(es), the elements of which are mounted with respect to one another in a temperature controlled mounting system, and the application thereof in focusing, (and/or colliminating), a spectroscopic electromagnetic beam into a very small, chromatically relatively undispersed, area spot on a material system. Said quasi-achromatic multi-element lens(es) preferably provide a relatively constant focal length at each wavelength in a large range of wavelengths, including in the visible and into the deep UV. Said present invention is based in the temperature controlled mounting system and method of its use in precisely providing a plurality of lenses with respect to one another therein.

BACKGROUND

It is known that generally, lens characteristics change with temperature. For instance thermal expansion of lens mounting can induce birefringence in a lens mounted therewithin. In addition to values of birefringence, focal length and spot size of a beam of electromagnetic radiation, where it is focused onto a sample, can change with temperature.

It would therefore be of value if a system comprising at least one lens element and a means for controlling the temperature thereof, were available. Said system would be even more valuable if the lens were mounted in a mounting means that changes shape with temperature in a manner such that stresses are not induced in the lens element by interaction therewith.

Such a temperature controlled mounted lens systems would find very relevant application in ellipsometer, polarimeter and the like systems. With that in mind it is disclosed that the practice of ellipsometry is well established as a non-destructive approach to determining characteristics of material systems, and can be applied in real time process control as well as ex-situ. The topic is generally well described in a number of publication, one such publication being a review paper by Collins, titled "Automatic Rotating Element Ellipsometers: Calibration, Operation and Real-Time Applications", Rev. Sci. Instrum, 61(8) (1990).

In general, modern practice of ellipsometry typically involves causing a spectroscopic beam of electromagnetic radiation, in an imposed, known, state of polarization, to interact with a material system at one or more angle(s) of incidence with respect to a normal to a surface thereof, in a plane of incidence. (Note, a plane of incidence contains both a normal to a surface of an investigated material system and the locus of said beam of electromagnetic radiation). Changes in the polarization state of said beam of electromagnetic radiation which occur as a result of said interaction with said material system are indicative of the structure and composition of said material system. The practice of ellipsometry utilizes said changes in polarization state by proposing a mathematical model of the ellipsometer system and the material system investigated by use thereof, obtaining experimental data by application of the ellipsometer system, and applying square error reducing mathematical regression, (typically), to the end that parameters in the mathematical model which characterize the material system are evaluated so that the obtained experimental data, and values calculated by use of the mathematical model have a "best match" relationship.

A goal in ellipsometry is to obtain, for each wavelength in, and angle of incidence of said beam of electromagnetic radiation caused to interact with a material system, material system characterizing PSI and DELTA values, (where PSI is related to a change in a ratio of magnitudes of orthogonal components $r_p/r_s$ in said beam of electromagnetic radiation, and wherein DELTA is related to a phase shift entered between said orthogonal components $r_p$ and $r_s$, caused by interaction with said material system. Said PSI and DELTA are defined by:

$$r_p/r_s = \mathrm{TAN}(\mathrm{PSI})\mathrm{EXP}^{(i\,DELTA)}.$$

As alluded to, the practice of ellipsometry requires that a mathematical model be derived and provided for a material system and for the ellipsometer system being applied. In that light it must be appreciated that an ellipsometer system which is applied to investigate a material system is, generally, sequentially comprised of:
  a. a Source of a beam electromagnetic radiation;
  b. a Polarizer element;
  c. optionally a compensator element;
  d. (additional element(s) such as lens(es), beam directing means, and/or windows such as in vacuum chambers);
  e. a material system;
  f. (additional element(s) such as lens(es), beam directing means, and/or windows such as in vacuum chambers);
  g. optionally a compensator element;

h. an Analyzer element; and i. a Detector System.

Each of said components b.-i. must be accurately represented by a mathematical model of the ellipsometer system along with a vector which represents a beam of electromagnetic radiation provided from said source of a beam electromagnetic radiation, Identified in a. above). (Note that elements (a-d) can be referred to a a Polarization State Generator (PSG), and elements (f-i) as a Polarization State Detector (PSD)).

Various ellipsometer configurations provide that a Polarizer, Analyzer and/or Compensator(s) can be rotated during data acquisition, and are describe variously as Rotating Polarizer (RPE), Rotating Analyzer (RAE) and Rotating Compensator (RCE) Ellipsometer Systems.

Where an ellipsometer system is applied to investigate a small region of a material system present, it must be appreciated that the beam of electromagnetic radiation can be convergently entered thereto through an input lens, and, optionally, exit via a re-collimating output lens. It is also possible to have only a collimating lens after the sample. In effect this adds said input, and/or output lens(es) as elements in the ellipsometer system as "additional elements", (eg. identified in d. and f. above), which additional elements must be accounted for in the mathematical model. If this is not done, material system representing parameters determined by application of the ellipsometer system and mathematical regression, will have the effects of said input, (and output), lenses at least partially correlated thereinto, much as if the input and, (output lenses), were integrally a part of the material system. Where two sequentially adjacent elements in an ellipsometer system are held in a static position with respect to one another while experimental ellipsometric data is acquired, said two sequentially adjacent elements generally appear to be a single element. Hence, a beam directing element adjacent to a lens can appear indistinguishable from said lens as regards the overall effect of said combination of elements. In that light it is to be understood that present input and output lenses are normally structurally fixedly positioned and are not rotatable with respect to a material system present in use, thus preventing breaking correlation between parameters in equations for sequentially adjacent input and output lenses and an investigated material system by an element rotation technique. While correlation of parameters in mathematical equations which describe the effects of groupings of elements, (such as a compensator and an optional element(s)), can be tolerable, correlation between parameters in the mathematical model of an investigated material system and other elements in the ellipsometer system must be broken to allow obtaining accurate material system representing PSI and DELTA values, emphasis added. That is to say that correlation between parameters in equations in a mathematical model which describe the effects of a stationary compensator and a sequentially next located lens element, (eg. correlation between effects of elements c. and d. or between f. and g. identified above), in a beam of electromagnetic radiation might be tolerated to the extent that said correlation does not influence determination of material system describing PSI and DELTA values, but the correlation between parameters in equations which describe the effects of ellipsometer system components (eg. a., b., c., d., f., g., h. and i.), and equations which describe the effects of a present material system (eg. element e. above), absolutely must be broken to allow the ellipsometer system to provide accurate PSI and DELTA values for said material system. Application of ellipsometry to investigation of a material system present can then present a challange to users of ellipsometer systems in the form of providing a mathematical model for each of an input and output lens, and providing a method by which the effects of said input and output lenses can be separated from the effects of an investigated material system.

Another rather obvious solution to the identified problem is to provide input, and output, lenses which are absolutely birefringence-free, and transparent at all electromagnetic beam wavelengths utilized. That is, provide input, and output, lenses which do not attenuate the magnitude of $r_p$ or $r_p$ orthogonal components, (or at least do not change their ratio, $r_p/r_s$), and which also do not enter phase shift between $r_p$ or $r_s$ orthogonal components when said beam of electromagnetic radiation is caused to pass therethrough. While control of the effect of a lens on a ratio, $(r_p/r_s)$, of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc. A system which would reduce birefringence in a lens by reducing temperature change then would provide utility.

As described in Parent application Ser. No. 09/162,217, (which is incorporated herein by reference), controlling stress related change is presently achieved with varying degrees of success, where for instance, windows in a vacuum chamber are subject. Windows provided by BOMCO Inc. are produced with the goal of eliminating birefringence, and are mounted in vacuum chambers using copper gasket seals which help to minimize uneven application of stresses and developed strains thereacross. While some success is achieved via this approach, the BOMCO windows are not "perfect" and do demonstrate some remaining birefringence properties, which can vary in unpredictable ways over a period of usage. Thus, even BOMCO windows can benefit from stress reducing systems, such as temperature control. BOMCO windows, however, are expensive, costing on the order of $1000.00 each), and are large in size thereby making adaptation thereof to use in a vacuum chamber difficult at times, particularly in retro-fit scenarios. And, there have been cases where BOMCO windows have broken in use. This is highly undesirable as vacuum chambers are often times caused to contain highly toxic and hazardous materials during, for instance, etching and/or deposition steps required in the fabrication of semiconductor devices. Where vacuum chamber windows are the subject, an alternative to use of the BOMCO windows is to simply use standard vacuum chamber windows, which, while significantly less expensive, demonstrate order of magnitude larger birefringence effects. (Note, BOMCO windows provide birefringent effects on the order of approximately six-tenths (0.6) to two-tenths (0.2) degrees over a range of wavelengths of from four-hundred (400) to seven-hundred-fifty (750) nanometers, whereas standard vacuum windows demonstrate birefringent effects on the order of six (6.0) to three (3.0) degrees over the same range of wavelengths). (Note, birefringent retardation typically follows an approximate inverse wavelength, (eg. 1/wavelength), relationship). However, where standard vacuum chamber windows are utilized, compensation of their effects is required. Similar concerns apply where input and output lenses, and associated ellipsometrically indistinguishable ellipsometer system components are concerned.

Patents and/or Published Applications which describe the use of multiple element lenses in Ellipsometer and the like systems include:

Applications of Danner et al.:
  EP1 172 642 A2;
  JAPAN 2002 209859 A
  US 2002/0024669;

Applications:
  WO 91/14157;
  WO 92/12404 by Rudolf Corp.;
  96/18205;
  WO 99/02950;

Patents:
  U.S. Pat. No. 4,671,657 to Calvani et al.;
  U.S. Pat. No. 5,166,752 to Spanier et al.;
  U.S. Pat. No. 5,349,497 to Morris;
  U.S. Pat. No. 5,877,859;
  U.S. Pat. No. 5,963,327 to He et al.;
  U.S. Pat. No. 5,978,087 to Patterson et al.
  Japanese Application H6 (1994)-22332.

Other patents of which the Inventor is aware include those to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertain to ellipsometer systems.

Additional patents of which the Inventor is aware include U.S. Pat. Nos. 5,757,494 and 5,956,145 to Green et al., in which are taught a method for extending the range of Rotating Analyzer/Polarizer ellipsometer systems to allow measurement of DELTA'S near zero (0.0) and one-hundred-eighty (180) degrees, and the extension of modulator element ellipsometers to PSI'S of forty-five (45) degrees. Said patents describes the presence of a variable, transmissive, bi-refringent component which is added, and the application thereof during data acquisition to enable the identified capability.

A patent to Thompson et al. U.S. Pat. No. 5,706,212 teaches a mathematical regression based double fourier series ellipsometer calibration procedure for application, primarily, in calibrating ellipsometers system utilized in infrared wavelength range. Birefringent window-like compensators are described as present in the system thereof, and discussion of correlation of retardations entered by sequentially adjacent elements which do not rotate with respect to one another during data acquisition is described therein.

A patent to Woollam et al, U.S. Pat. No. 5,582,646 is disclosed as it describes obtaining ellipsometic data through windows in a vacuum chamber, utilizing other than a Brewster Angle of Incidence.

Patent to Woollam et al, U.S. Pat. No. 5,373,359, patent to Johs et al. U.S. Pat. No. 5,666,201 and patent to Green et al., U.S. Pat. No. 5,521,706, and patent to Johs et al., U.S. Pat. No. 5,504,582 are disclosed for general information as they pertian to Rotating Analyzer ellipsometer systems. The 359 patent describes a Rotating Analyzer Ellipsometer (RAE) which can comprise a Collimating Lens prior to the Sample being investigated, but has no Lens after said Sample. While not specifically disclosing a focusing lens before the Sample and no collimating lens thereafter, said 359 patent does obviate the use of a lens before a sample in an ellipsometer, with no lens after said sample being present.

Patents identified in a Search specifically focused on the use of lenses, preferrably achromatic, in ellipsometry and related systems are:
  U.S. Pat. Nos. 5,877,859 and 5,798,837 to Aspnes et al.;
  U.S. Pat. No. 5,333,052 to Finarov;
  U.S. Pat. No. 5,608,526 to Piwonka-Corle et al.;
  U.S. Pat. No. 5,793,480 to Lacy et al.;
  U.S. Pat. Nos. 4,636,075 and 4,893,932 to Knollenberg; and
  U.S. Pat. No. 4,668,860 to Anthon.

Another patent found is U.S. Pat. No. 5,917,594 to Norton. The system disclosed therein utilizes a spherical mirror to focus an electromagnetic beam onto the surface of a sample in the form of a small spot. Said system further develops both reflection and transmission signals via application of reflective means and of reflection and transmission detectors. The somewhat relevant aspect of the 594 patent system is that a positive lens and a negative meniscus lens are combined and placed into the pathway of the electromagnetic beam prior to its reflection from a focusing spherical mirror. The purpose of doing so is to make the optical system, as a whole, essentially achromatic in the visible wavelength range, and even into the ultraviolet wavelength range. It is further stated that the power of the combined positive lens and negative meniscus lens is preferrably zero. It is noted that, as described elsewhere in this Specification, said 594 patent lens structure, positioning in the 594 patent system, and purpose thereof are quite distinct from the present invention lens structure and application to focus a beam of electromagnetic radiation.

A patent to He et al., U.S. Pat. No. 5,963,327 is disclosed as it describes an ellipsometer system which enables providing a polarized beam of electromagnetic radiation at an oblique angle-of-incidence to a sample system in a small spot area.

A patent to Johs et al., U.S. Pat. No. 5,872,630 is disclosed as it describes an ellipsometer system in which an analyzer and polarizer are maintained in a fixed in position during data acquisition, while a compensator is caused to continuously rotate.

Patent to Dill et al., U.S. Pat. No. 4,953,232 is disclosed as it describes a rotating compensator ellipsometer system.

Patents co-owned with this application, which patents Claim various Compensator Designs recited in Claims herein, and which Patents are incorporated hereinto by reference are:
  U.S. Pat. No. 5,946,098 to Johs et al.;
  U.S. Pat. No. 5,963,325 to Johs et al.;
  U.S. Pat. No. 6,084,674 to Johs et al.;
  U.S. Pat. No. 6,084,675 to Herzinger et al.;
  U.S. Pat. No. 6,100,981 to Johs et al.;
  U.S. Pat. No. 6,118,537 to Johs et al.;
  U.S. Pat. No. 6,141,102 to Johs et al.

Patents cited in examination of said patents included U.S. Pat. No. 4,556,292 to Mathyssek et al. and U.S. Pat. No. 5,475,525 to Tournois et al.

A patent to Bjork et al., U.S. Pat. No. 4,647,207 is disclosed as it describes an ellipsometer system which has provision for sequentially positioning a plurality of reflective polarization state modifiers in a beam of electromagnetic radiation. While said 207 patent mentions investigating a sample system in a transmission mode, no mention or suggestion is found for utilizing a plurality of transmitting polarization state modifiers, emphasis added. U.S. Pat. Nos. 4,210,401; 4,332,476 and 4,355,903 are also identified as being cited in the 207 patent. It is noted that systems as disclosed in these patents, (particularly in the 476 patent), which utilize reflection from an element to modify a polarization state can, that if such an element is an essential duplicate of an investigated sample and is rotated ninety degrees therefrom, then the effect of the polarization state modifying element on the electromagnetic beam effect is extinguished by the sample.

Patents to Rosencwaig et al., U.S. Pat. Nos. 4,750,822 and 5,595,406 are also identified as they describe systems which impinge electromagnetic beams onto sample systems at oblique angles of incidence. The 406 patent provides for use of multiple wavelengths and multiple angles of incidence. For similar reasons U.S. Pat. No. 5,042,951 to Gold et al. is also disclosed.

A patent to Osterberg, U.S. Pat. No. 2,700,918 describes a microscope with variable means for increasing the visibility of optical images, partially comprised of discrete bi-refringent plates which can be positioned in the pathway between an eyepiece and an observed object. Other patents identified in a Search which identified said 918 patent are U.S. Pat. No. 3,183,763 to Koester; U.S. Pat. No. 4,105,338 to Kuroha; U.S. Pat. No. 3,992,104 to Watanabe and a Russian Patent, No. SU 1518728. Said other patents are not believed to be particularly relevant, however.

A patent, U.S. Pat. No. 5,329,357 to Bernoux et al. is also identified as it Claims use of fiber optics to carry electromagnetic radiation to and from an ellipsometer system which has at least one polarizer or analyzer which rotates during data acquisition. It is noted that if both the polarizer and analyzer are stationary during data acquisition that this patent is not controlling where electromagnetic radiation carrying fiber optics are present.

A patent to Chen et al., U.S. Pat. No. 5,581,350, is disclosed as it describes a method for regression calibration of ellipsometers which is very much similar to that disclosed earlier in an article by Johs.

Patent to Wang. et al., U.S. Pat. No. 6,587,282 is disclosed as it describes a three lens system with specific curvature and spacings associated with each of the lenses.

Patent to Uhrich et al., U.S. Pat. No. 6,829,049 is disclosed as it describes a broadband ellipsometer with all refractive optical system for focusing a probe beam onto a sample.

As present invention preferred practice is to utilize a spectroscopic source of electromagnetic radiation with a relatively flat spectrum over a large range of wavelengths U.S. Pat. No. 6,628,917 to Johs is disclosed. Patents relevant thereto include U.S. Pat. No. 5,179,462 to Kageyama et al. is identified as it provides a sequence of three electromagnetic beam combining dichroic mirrors in an arrangement which produces an output beam of electromagnetic radiation that contains wavelengths from each of four sources of electromagnetic radiation. Each electromagnetic beam combining dichroic mirror is arranged so as to transmit a first input beam of electromagnetic radiation, comprising at least a first wavelength content, therethrough so that it exits a second side of said electromagnetic beam combining dichroic mirror, and to reflect a second beam of electromagnetic radiation, comprising an additional wavelength content, from said second side of said electromagnetic beam combining dichroic mirror in a manner that a single output beam of electromagnetic radiation is formed which contains the wavelength content of both sources of electromagnetic radiation. The sources of electromagnetic radiation are described as lasers in said 462 patent. Another patent, U.S. Pat. No. 5,296,958 to Roddy et al., describes a similar system which utilizes Thompson Prisms to similarly combine electromagnetic beams for laser source. U.S. Pat. Nos. 4,982,206 and 5,113,279 to Kessler et al. and Hanamoto et al. respectively, describe similar electromagnetic electromagnetic beam combination systems in laser printer and laser beam scanning systems respectively.

Another patent, U.S. Pat. No. 3,947,688 to Massey, describes a method of generating tuneable coherent ultraviolet light, comprising use of an electromagnetic electromagnetic beam combining system. A patent to Miller et al., U.S. Pat. No. 5,155,623, describes a system for combining information beams in which a mirror comprising alternating regions of transparent and reflecting regions is utilized to combine transmitted and reflected beams of electromagnetic radiation into a single output beam. A patent to Wright, U.S. Pat. No. 5,002,371 is also mentioned as describing a beam splitter system which operates to separate "P" and "S" orthogonal components in a beam of polarized electromagnetic radiation.

Various papers were also identified as possibly pertinent, and are:

A paper by Johs, titled "Regression Calibration Method for Rotating Element Ellipsometers", Thin Solid Films, 234 (1993) is also disclosed as it describes a mathematical regression based approach to calibrating ellipsometer systems.

A paper by Nijs & Silfhout, titled "Systematic and Ramdom Errors in Rotating-Analyzer Ellipsometry", J. Opt. Soc. Am. A., Vol. 5, No. 6, (June 1988), describes a first order mathematical correction factor approach to accounting for window effects in Rotating Analyzer ellipsometers.

A paper by Kleim et al, titled "Systematic Errors in Rotating-Compensator ellipsometry", J. Opt. Soc. Am., Vol 11, No. 9, (setp. 1994) describes first order corrections for imperfections in windows and compensators in Rotating Compensator ellipsometers.

Other papers of interest in the area by Azzam & Bashara include one titled "Unified Analysis of Ellipsometry Errors Due to Imperfect Components Cell-Window Birifringence, and Incorrect Azimuth Angles", J. of the Opt. Soc. Am., Vol 61, No. 5, (May 1971); and one titled "Analysis of Systematic Errors in Rotating-Analyzer Ellipsometers", J. of the Opt. Soc. Am., Vol. 64, No. 11, (November 1974).

Another paper by Straaher et al, titled "The Influence of Cell Window Imperfections on the Calibration and Measured Data of Two Types of Rotating Analyzer Ellipsometers", Surface Sci., North Holland, 96, (1980), describes a graphical method for determining a plane of incidence in the presence of windows with small retardation.

A paper by Jones titled "A New Calculus For The Treatment Of Optical Systems", J.O.S.A., Vol. 31, (July 1941), is also identified as it describes the characterizing of multiple lens elements which separately demonstrate birefringence, as a single lens, (which can demonstrate reduced birefringence).

A paper by Zapien et al., titled: "Real-Time Spectroscopic Ellipsometry from 1.5 to 6.5 eV", Thin Solid Films 364, (2000), shos lenses on both sides of a sample.

A paper by Li titled: "Flying Height Measurementon Al2O3 Film of a Magnetic Slider", J. or Tribiology, (October 1997) describes a 17 micron spot size achieved by a focusing lens.

A paper by Ghazzawl et al., titled: "Spectroellipsometry Characterization of Directly Bonded Silicon-On-Insulator Structures: Thin Solid Films 233 (1993).

Finally, a paper which is co-authored by inventors herein is titled "In Situ Multi-Wavelength Ellipsometric Control of Thickness and Composition of Bragg Reflector Structures", by Herzinger, Johs, Reich, Carpenter & Van Hove, Mat. Res. Soc. Symp. Proc., Vol. 406, (1996) is also disclosed.

Even in view of relevant prior art, there remains need for a system for controlling the temperature of lenses. Relevant application is in ellipsometer systems which comprise input, and optionally output, lenses that allow focusing spectroscopic electromagnetic beams as small spots on material substrates.

Need remains for a lens system, and the method of its construction, which enables very precise lens characteristics realization and control over temperature caused effects.

The present invention provides a system with the identified attributes.

DISCLOSURE OF THE INVENTION

The present invention provides that a temperature control system be provided which can be applied to control the temperature of at least one lens element, and the preferred embodiment of the present invention provides that multiple lens elements be mounted in a tube. Said tube can have at least one hole through the wall thereof such that cement is applied through said at least one hole to secure at least one of said lenses or lens elements in place therewithin.

The disclosed invention is an ellipsometer or polarimeter system comprising at least one multi-element lens placed at a selection from the group consisting of:
 at the input; and
 at the output;
said at least one multi-element lens being comprised of at least two elements which are made of different materials, such that in use the focal length for each wavelength in a range of wavelengths is essentially the same for every other wavelength is said range of wavelengths;
said ellipsometer or polarimeter system further comprising a temperature control system for controlling the temperature of at least one lens element and mounting therefore.

Preferred construction of said at least one multi-element lens provides three elements:
 Calcium Fluoride;
 Fused Silica;
 Calcium Fluoride;
said elements being cemented to a mounting system instead of said Calcium Fluoride-Fused Silica-Calcium Fluoride elements being mounted to a lens mounting system which minimizes stress on the three lenses, in order to minimize stress induced birefringence.

Said ellipsometer or polarimeter can further comprise a broadband source for generating a polychromatic probe beam and a polarizer prior to a sample; and an analyzer and detector after said sample, and in the case of a polarimeter, at least one compensator is present at, at least one location selected from the group consisting of:
 before said sample; and
 after said sample.

The disclosed invention can be described as a broadband ellipsometer or polarimeter system for evaluating the characteristics of a sample comprising:
 a broadband light source for generating a polychromatic probe beam, said polychromatic probe beam comprising at least UV and Visible wavelengths; an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium fluoride and fused silica, said lenses being present in a tube which comprises at least one hole through the wall thereof for accepting cement; such that at least first said lens is placed in said tube at the location of a hole for accepting cement and cement is entered thereinto and allowed to dry, thereby securing said lens in place in said tube; and such that an additional lens is mounted by a selection from the group consisting of:
 being similarly cemented into place in said tube at a precise location with respect to said first lens; and
 being positioned in said tube with respect to said first lens in a stress reducing manner comprising spacer means for maintaining relative position between said lenses;

said broadband ellipsometer or polarimeter system further comprising an analyzer system for monitoring at least a portion of a probe beam reflected from said sample, and generating output signals responsive thereto, and a processor for evaluating characteristics of the sample based on the output signals; and a temperature control system which can be applied to control the temperature of at least one lens element.

Said broadband ellipsometer or polarimeter system can comprise three lenses present in said tube, each thereof being located with respect to holes through the wall of said tube and secured in said position by cement which is entered into said holes. A preferred arrangement of lenses provides that bi-convex converging calcium fluoride lenses disposed be opposite sides of a bi-concave diverging fused silica lens.

The disclosed invention also includes a method of improving the operation of a broadband ellipsometer or polarimeter for evaluating the characteristics of a sample comprising:
 a) providing broadband ellipsometer or polarimeter which comprises:
 broadband light source means for generating a polychromatic probe beam, said polychromatic probe beam comprising at least UV and Visible wavelengths;
 an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium fluoride and fused silica, said lenses being present in a tube which comprises holes through the wall thereof for accepting cement;

said broadband ellipsometer or polarimeter further comprising a temperature control system which can be applied to control the temperature of at least one lens element;
 b) effecting the relative position between at least two of said at least two lenses in said tube by, while actively monitoring of the effect of said at least two lenses on a beam of electromagnetic radiation caused to pass therethrough, adjusting said relative position until an acceptable effect is achieved on said electromagnetic beam, and wherein cement is then entered through holes in the wall of said tube which are near edges of said at least two lenses, to secure the positions of said lenses;

such that said at least two lenses are precisely secured in said tube at desired locations relative to one another; and
 c) applying said temperature control system to control the temperature of at least one lens element.

Said method can be practiced where there are three lenses present in said tube, each thereof being precisely located with respect to one another and secured in said position by cement which is entered into said holes through the wall of said tube when an acceptable effect on said beam of electromagnetic radiation is achieved. Said three lenses which are precisely positioned with respect to one another are preferably two convex calcium fluoride lenses disposed on opposite sides of a fused silica lens.

Further, there can four, or any number of lenses present.

A broadband ellipsometer or polarimeter for evaluating the characteristics of a sample can then be recited as comprising: a broadband light source for generating a polychromatic probe beam, said polychromatic probe beam comprising at least UV and Visible wavelengths, an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium fluoride and fused silica, said lenses being present in a tube which comprises holes through the wall thereof for accepting cement;

such that lenses are placed in said tube at the location of said holes for accepting cement and cement is entered thereinto and allowed to dry, thereby securing said lenses in place;

said broadband ellipsometer or polarimeter system further comprising an analyzer system for monitoring at least a portion of a probe beam reflected from said sample and generating output signals responsive thereto, and a processor for evaluating characteristics of the sample based on said output signals;

said broadband ellipsometer or polarimeter being distinguished in that the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved on said beam of electromagnetic radiation, and wherein cement is then entered through at least one hole in the wall of said tube which is near an edge of at least one of said at least two lenses, to secure the positions of said lenses. All present lenses can be similarly secured in place in said tube, or at least one additional lens can be positioned with respect to a cemented in place lens via spacer means for effecting position between lenses in a stress reducing manner; and said broadband ellipsometer or polarimeter being further distinguished in that a temperature control system is present which can be applied to control the temperature of at least one lens element.

And again, said broadband ellipsometer or polarimeter can comprise, for instance, three lenses in which the relative position between the first and second, and between the second and third is precisely controlled prior to cementing them into position in said tube.

Where there are three lenses present having a combined focal length (F), the first lens can be a positive lens made from a first material, the second lens can be a negative lens made from a second material, and the third lens can be a positive lens made from a third material. Said three lenses can be considered to have "n" faces numbered 1-6, with "rn" being the radius of curvature of the nth face, and "tn" being the spacing nth and (n+1)st face. The preferred embodiment provides that at least one of said "r2" and/or "t4" be other than:

$r2 < F$;

$t4 > 0.05F$.

And at least one of said "r4" and/or "r5" can optionally be other than:

$r4 > 2.5F$ $r5 > 0.5F$.

As previously presented in a Parent application, the present invention system comprises a lens system, primarily as applied in ellipsometer and polarimeter systems wherein birefringence, and spectroscopic electromagnetic beam spot size chromatic dispersion reduction and focal length chromatic dispersion reduction is desired, but wherein spherical, coma distortion, third order aberations, astigmatism and image reproduction are of lesser importantance. A single stage present invention lens system can have a focal length of one-hundred millimeters or less, (nominally about eighty millimeters), and said lens system comprises two sequentially oriented elements, one of said two sequentially oriented elements being of a shape and orientation which individually converges a beam of electromagnetic radiation caused to pass therethrough, and the other being of a shape and orientation which individually diverges, (to a lesser degree than said convergence), a beam of electromagnetic radiation caused to pass therethrough, there being a region between said first and second elements. A present invention dual stage lens system provides a less than fifty millimeter, (nominal about forty millimeter), focal length and is comprised of four sequentially oriented lens elements which are grouped into two groups of two elements each, two of which four elements are converging and two of which are diverging of electromagnetic radiation caused to pass therethrough.

It is to be understood that, in use, a beam of electromagnetic radiation sequentially passes through one of said first and second elements in a single present invention lens system, then said region therebetween, and then through said second of said first and second elements before emerging as a focused beam of electromagnetic radiation, said region between said first and second elements have essentially the optical properties of a void region, or functional equivalent. In a dual stage present invention lens system a second stage of first and second elements is present in the electromagnetic beam pathway.

Further, present invention lens systems are characterized as quasi-achromatic as a result of multi-element construction, wherein, for each said two element lens systems present, the two elements thereof are made from different materials, (eg. one from what is commonly termed Crown-glass and one from Flint-glass in the literature). Again, as a result of present invention lens construction, very small electromagnetic beam spot focusing on an investigated material system is possible over a large range of wavelengths, (including transmitting properties into the deep UV), because of reduced chromatic focal length and spot size dispersion. It is noted that said present invention multi-element ellipsometer system input (and output) lenses can both (when present) demonstrate birefringence; neither demonstrate birefringence or one can demonstrate birefringence and the other not demonstrate birefringence. In fact, as disclosed in U.S. Pat. No. 6,549,282, Ser. No. 09/419,794 Filed Oct. 18, 1999, in Col. 13, Lines 34-37, one non-birefringent input or output lens can be absent but for a consideration of its presence as essentially surrounding atmospheric ambient, or equivalent thereto. That is, the concept of a multi-element focusing lens in an ellipsometer, without the presence of a recollimation lens therein, was disclosed in October 1999 by the present inventors, which is prior to the Filing Date of a patent to Uhrich et al., U.S. Pat. No. 6,829,049 which was Filed May 3, 2001 with Priority Claimed from 60/204,253 which was filed in the year 2000.

A present invention lens system, which is particularly well suited for application in ellipsometer systems, provides for spectroscopic electromagnetic beam spot size and focal length chromatic dispersion reduction by configuring at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation. Such a lens system with application in ellipsometer systems is characterized by a converging element which presents as a selection from the group consisting of:
  a bi-convex;
  a plano-convex with an essentially flat side;
and said diverging element is characterized as a selection from the group consisting of:
  a bi-concave lens element;
  a plano-concave with an essentially flat side.

Further said present invention lens systems can comprise a selection from the group consisting of:
  a) at least one thereof comprises:
    two sequentially oriented elements, one of said two sequentially oriented elements being of a shape and orientation which individually diverges a beam of electromagnetic radiation caused to pass therethrough, and the other being of a shape and orientation which individually converges a beam of electromagnetic radiation caused to pass therethrough,
    there being a region between said at least two elements such that, in use, a beam of electromagnetic radiation sequentially passes through one of said at least two elements, then said region therebetween, and then the other of said at least two elements before emerging as an effectively converged, focused, beam of electromagnetic radiation.
  b) at least one thereof comprises:
    a sequential combination of a bi-convex element and a bi-concave element.
  c) at least one thereof comprises:
    a sequential combination of a biconcave element and a bi-convex element.
  d) at least one thereof comprises:
    a sequential combination of a bi-convex element and a plano-concave element with said concave side of said plano-concave element adjacent to said bi-convex element.
  e) at least one thereof comprises:
    a sequential combination of a bi-convex element and a plano-concave element with said essentially flat side of said plano-concave element being adjacent to said bi-convex element;
  f) at least one thereof comprises:
    a sequential combination of a plano-concave element and a bi-convex element with said essentially flat side of said plano-concave element adjacent to said bi-concave element;
  g) at least one thereof comprises:
    a sequential combination of a plano-concave element and bi-convex element with said concave side of said plano-concave element adjacent to said bi-convex element;
  h) at least one thereof comprises:
    a sequential combination of a plano-convex element and a bi-concave element with said essentially flat side of said plano-convex element adjacent to said bi-concave element;
  i) at least one thereof comprises:
    a sequential combination of a bi-concave element with a plano-convex element with said convex side of said plano-convex element adjacent to said bi-concave element;
  j) at least one thereof comprises:
    a sequential combination of a plano-concave element and a plano-convex element with the essentially flat side of said plano-concave element being adjacent to the convex side of the plano-convex element;
  k) at least one thereof comprises:
    a sequential combination of a plano-concave element and a plano-convex element with the essentially flat side of said planoconcave element being adjacent to the flat side of said plano-convex element;
  l) at least one thereof comprises:
    a sequential combination of a plano-convex element and a plano-concave element with the essentially flat side of said plano-convex element and the essentially flat side of said plano-concave element being adjacent to one another;
  m) at least one thereof comprises:
    a sequential combination of a plano-concave element and a plano-convex element with the concave side of said plano-concave element being adjacent to the convex side of the plano-convex element;
  n) at least one thereof comprises:
    a sequential combination of a plano-convex element bi-concave element with said convex side of said plano-convex element adjacent to said bi-concave element;
  o) at least one thereof comprises:
    a sequential combination of a bi-concave element and a plano-convex element with said essentially flat side of said plano-convex element adjacent to said bi-concave element;
  p) at least one thereof comprises:
    a sequential combination of a plano-convex element and a plano-concave element with said convex side of said plano-convex element adjacent to the concave side of the plano-concave element;
  q) at least one thereof comprises:
    a sequential combination of a plano-concave element and a plano-convex element with said essentially flat side of said plano-concave element being adjacent to the essentially convex side of the plano-convex element;
  r) at least one thereof comprises:
    a sequential combination of a plano-convex element and a plano-concave element with said convex side of said plano-convex element being adjacent to the essentially flat side of the plano-concave element;
  s) at least one thereof comprises:
    a sequential combination of a plano-concave element with a plano-convex element with the essentially flat side of said plano-convex element being adjacent to the concave side of said plano-concave element;
  t) at least one thereof comprises:
    at least one of the input and output lenses comprises at least two sequentially oriented elements, and is characterized by being a selection from the group consisting of:
    a sequential combination of a converging element and a diverging element;
    a sequential combination of a diverging element and a converging element;

a sequential combination of a converging element, a diverging element, a converging element and a diverging element;

a sequential combination of a converging element, a diverging element, a diverging element and a converging element;

a sequential combination of a diverging element, a converging element, a diverging element and a converging element;

a sequential combination of a diverging element, a converging element, a converging element and a diverging element;

includes a miniscus lens; and includes an aspherical lens;

u) at least one thereof comprises:
two elements with a region therebetween, wherein said region between said at least two elements has the optical properties of a selection from the group consisting of:
a void region; and
a functional equivalent to a void region;

v) at least one thereof comprises:
at least two elements which are made from different materials independently selected from the group consisting of:
$CaF_2$;
$BaF_2$;
LiF;
$MgF_2$;
fused silica;
a void region;
a gas filled region;
a liquid filled region; and
a functional equivalent to a void region.

and wherein each of said at least two elements are individually selected to be made of different materials;

w) at least one thereof is characterized by at least one selection from the group consisting of:
a) the focal length is between forty and forty-one millimeters over a range of wavelengths of at least two-hundred to seven-hundred nanometers;
b) the focal length varies by less than five (5%) percent over a range of wavelengths of between two-hundred and five-hundred nanometers; and
c) the spot diameter at the focal length is less than seventy-five microns over a range of wavelengths of at least two-hundred to seven-hundred nanometers;

x) at least one thereof comprises:
an element made of a selection from the group consisting of:
$CaF_2$; and
fused silica;

y) at least one thereof:
is made of two elements, one of said elements being made of Fused Silica and the other of $CaF_2$;

z) at least one thereof comprises:
a converging element selected from the group consisting of:
a positive miniscus;
an asymetric convex;

and/or a diverging element selected from the group consisting of:
a negative miniscus;
an asymetric concave.

A present invention lens system with application in ellipsometer systems can be further characterized in that the converging element of said first and second elements is typically made of a material independently selected from the group consisting of:
$CaF_2$;
$BaF_2$;
LiF; and
$MgF_2$;
fused silica;
a void region;
a gas filled region;
a liquid filled region; and
a functional equivalent to a void region.

and the diverging element of said first and second elements is selected to be made of fused silica, although it is within the scope of the present invention to make the converging element of fused silica and the diverging element of a selection from the group consisting of $CaF_2$; $BaF_2$; LiF; and $MgF_2$. It is noted that lens elements made of $MgF_2$ are typically bi-refringent whereas lens elements made of $CaF_2$; $BaF_2$ and LiF typically demonstrate far less bi-refringence, unless subjected to stress.

A present invention lens system with a focal length of fifty millimeters or less, with application in ellipsometer systems, can be described as being comprised of lens system comprising two sequentially oriented lenses, each of said sequentially oriented lenses being comprised of:

at least two sequentially oriented elements, one of said at least two sequentially oriented elements being of a shape and orientation which individually converges a beam of electromagnetic radiation caused to pass therethrough, and the other being of a shape and orientation which individually diverges a beam of electromagnetic radiation caused to pass therethrough, there being a region between said first and second elements such that, in use, a beam of electromagnetic radiation sequentially passes through said first element, then said region therebetween, and then said second element before emerging as a focused beam of electromagnetic radiation; said lens system being described by a selection, as shown in FIGS. 1*a*25-1*a*28, from the group consisting of:

1. a sequential combination of a converging element (C), a diverging element (D), a converging element (C) and a diverging element (D);

2. a sequential combination of a converging element (C), a diverging (D) element, a diverging (D), element and a converging (C) element;

3. a sequential combination of a diverging element (D), a converging element (C), a diverging (D) element and a converging (C) element;

4. a sequential combination of a diverging element (D), a converging element (C), a converging element (C) and a diverging (D) element.

And, of course, other sequential lens element configurations within the scope of the present invention include:

(Converging(C))(Diverging(D))(Converging(C));
(Converging(C))(Converging(C))(Diverging(D));
(Diverging(D))(Diverging(D))(Converging(C));
(Converging(C)) (Diverging(D))(Diverging(D));
(Diverging(D))(Converging(C))(Diverging(D));
(Converging(C))(Converging(C))(Diverging(D))(Diverging(D)); and (Diverging(D))(Diverging(D))(Converging(C))(Converging(C)).

One embodiment of a present invention lens system is further characterized by at least one selection from the group consisting of:

a. the focal length of the lens system is between forty (40) and forty-one (41) millimeters over a range of wavelengths of at least two-hundred (200) to seven-hundred (700) nanometers; and b. the focal length of the dual stage lens system varies by less than five (5%) percent over a range of wavelengths of between two-hundred and five-hundred nanometers; and c. the spot diameter at the focal length of the lens system is less than seventy-five (75) microns over a range of wavelengths of at least two-hundred (200) to seven-hundred (700) nanometers.

(It is noted that the listing of single two element lens constructions (a) through (r) above provides insight to applicable converging and diverging lens element combinations in dual stage lens systems).

It is specifically noted that the present invention includes the case of an ellipsometer system in which only one of said multi-element input or output lenses is present, (typically only the input lens), and the case wherein both input and output lenses are present, but only one is of multiple element construction, and/or demonstrates bi-refringence.

A preferred present invention single two element lens system is constructed from a Bi-convex lens element made of $CaF_2$, (eg. JANOS Technology Inc. Part No. A1407-003), functionally combined with a Fused Silica Plano-Concave lens element, (eg. OptoSigma Inc. Part No. 012-0080), in a manner generally indicated by FIG. 1a3.

In any of the forgoing examples, it should be appreciated that the present invention provides that a temperature control system is present which can be applied to control the temperature of at least one lens element, and that when applied said at least one multiple element lens is present at least one location in an ellipsometer or polarimeter system selected from the group consisting of:

between said polarizer and said stage for supporting a sample system; and between said stage for supporting a sample system and said analyzer;

and positioned so that said beam of electromagnetic radiation transmits therethrough in use typically comprises at least two elements which are made from different materials, such that in use the focal length for each wavelength in a range of wavelengths is within an acceptable range of focal lengths.

It is generally presented that achromatic lens systems are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently.

Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

It is also noted that ideal lenses do not attenuate the magnitude of $r_p$ or $r_s$ orthogonal components, (or at least do not change their ratio, $r_p/r_s$), and also do not enter phase shift between $r_p$ or $r_s$ orthogonal components when said beam of electromagnetic radiation is caused to pass therethrough. While control of the effect of a lens on a ratio, $(r_p/r_s)$, of electromagnetic beam orthogonal components can often rather successfully be accomplished by causing a beam of electromagnetic radiation to approach a surface of a lens along essential a normal to a surface thereof, this is not the case regarding phase shift entered between $r_p$ and $r_s$ orthogonal components of a said beam of electromagnetic radiation caused to pass therethrough. That is, input, and output, lenses can demonstrate "birefringence", in that the $r_p$ orthogonal component is "retarded" by a different amount than is the $r_s$ orthogonal component when said beam of electromagnetic radiation is caused to pass therethrough. To complicate matters, this "birefringent" effect also varies with wavelength and with stresses which can develop in a lens during use because of temperature and physical changes etc.

In summary, the present invention discloses that multi-element lenses can be produced that provide essentially constant focal lengths and small spot size over a large spectroscopic range of wavelengths, and that said multi-element lenses can be produced which demonstrate small birefringence, and that a temperature control system positioned to control the temperature of at least one lens element can be applied to reduce birefringence effects, and maintain focal length and/or spot size of a beam of electromagnetic radiation.

With the just recited listing of lens construction in mind, it should be appreciated that the disclosed invention can comprise a spectroscopic ellipsometer sequentially comprising:

a) a source of a spectroscopic beam electromagnetic radiation;

b) a polarizer element;

in either order elements c and d:
c) optionally a compensator element;
d) said input lens;
e) a material system;

in either order elements f and g:
f) said output lens;
g) optionally a compensator element;
h) an analyzer element; and
i) a detector System;

wherein at least one of the input and output lenses has associated therewith a temperature control system which can be applied to control the temperature of at least one lens element thereof.

Said input or output lens can comprise at least one multiple element lens formed from at least two elements which are made from different materials independently selected from the group consisting of:
$CaF_2$;
$BaF_2$;
LiF;
$MgF_2$;
fused silica;
a void region;
a gas filled region;
a liquid filled region; and
a functional equivalent to a void region.

The present invention approach is then to strive to avoid stress-induced birefringence in lens(es) mounted in an ellipsometer or polarimeter system by controlling the temperature of at least one element of a multi-element lens, which is preferably mounted in a tube in a multiple lens element configuration and to improve consistency in focal length and spot size of an electromagnetic beam where it impinges on a sample.

The present invention will be better understood by reference to the Detailed Description Section of this Disclosure, with appropriate reference being has to the Drawings.

SUMMARY OF THE INVENTION

It is a primary purpose and/or purpose of the present invention to teach a lens system which comprises a means for controlling the temperature of a lens therein.

It is another purpose and/or purpose of the present invention to teach a temperature controlled multi-element lens system which comprises a plurality of lenses mounted in a tube, at least one of which is held in place by cement or other firm securing means which is applied via the wall of said tube.

It is another objective and/or purpose of the present invention to describe a temperature controlled lens system which enables practice of focused beam small-spot spectroscopic ellipsometry over a large wavelength range, including in the visible and into the deep UV, (eg. wavelengths down to and below 190 NM). Multi-element lenses which comprise elements made of different materials allow essentially the same focal length to be achieved over a wide wavelength range.

It is yet another objective and/or purpose of the present invention to provide a method of precisely controlling the temperature of a lens by application of a feedback system.

Other objectives and/or purposes will become apparent by reference to other sections of this Specification.

BRIEF DESCRIPTION OF THE DRAWINGS

FIG. 1a1 shows a general elemental configuration of an ellipsometer system which can be applied to investigate a material system (SS).

FIG. 1a2 shows a perspective view of another ellipsometer system configuration showing the presence of electromagnetic beam directing optical elements (PRI) and (PRO).

FIG. 1a3 shows construction of a quasi-achromatic multi-element lens which can be considered as present at AC1 or AC2 in FIG. 1a1.

FIG. 1a4 shows construction of a dual stage quasi-achromatic multi-element lens which can be considered as present at AC1 or AC2 in FIG. 1a1.

FIG. 1a5 shows a plot of spot diameter vs. wavelength which characterizes a dual stage quasi-achromatic multi-element lens as shown in FIG. 1a4, and of single stage fused silica and CaF$_2$ lenses.

FIG. 1a6 shows a plot of focal length vs. wavelength which characterizes a dual stage quasi-achromatic multi-element lens as shown in FIG. 1a4, and of single stage fused silica and CaF$_2$ lenses.

FIGS. 1a7-1a24 show various combinations of bi-concave, plano-concave, bi-convex and plano-convex lens elements which can comprise a present invention lens.

FIGS. 1a25-1a28 show various sequences of converging and diverging lens elements which can comprise a present invention dual lens system.

DETAILED DESCRIPTION

Turning now to the Drawings, there is shown in FIG. 1a1, a general elemental configuration of an ellipsometer system to which the present invention can be applied to investigate a material system (SS). Shown for reflection and transmission are:

a. a Source of a beam electromagnetic radiation (LS);
b. a Polarizer element (P);
c. optionally a compensator element (C1);
d. (additional element(s)) (AC1);
e. a material system (SS);
f. (additional element(s)) (AC2);
g. optionally a compensator element (C2);
h. an Analyzer element (A); and
i. a Detector System (DET).

The elements identified as (LS), (P) and (C1) can be considered to form, as a group, a Polarization State Generator (PSG), and the components (C2), (A) and (DET) can be considered, as a group, to form a Polarization State Detector (PSD). It is to be understood that the d. and f. "additional elements", (AC1) and (AC2), can be considered as being, for the purposes of the present Invention Disclosure, primarily input and output lenses, and that only one such lens might be present in an ellipsometer system, (typically the input lens (AC1)). FIG. 1a3 shows the preferred construction of a present invention single quasi-achromatic multi-element lens which can be considered as present at AC1 or AC2. Note the presence of two (2) lens elements (FE1) and (FE3), with FE2 being a third lens element, or a void or "air gap", or a material with functionally similar optical properties. FIG. 1a4 shows the construction of a present invention dual quasi-achromatic multi-element lens which can be considered as present at AC1 or AC2, with an element sequence of:

((Diverging(D))(Converging(C))(Converging (C))(Diverging(D));

as indicated in FIG. 1a28. In FIG. 1a4, it is to be understood that one, or both, of the two quasi-achromatic multi-element lens shown can be reversed left to right, (ie. replaced with a vertical mirror image), and remain within the scope of the present invention. Another embodiment provides that a sequence of lens elements be:

(Converging(C))(Diverging(D))(Converging (C))(Diverging(D));

as indicated in FIG. 1a25, which is achieved by providing a vertically oriented mirror image of the first lens system which is comprised of (FE1a) (FE2a) and (FE3a) in FIG. 1a4. Other arrangements are indicated in FIGS. 1a26 and 1a27.

Figure 2A:
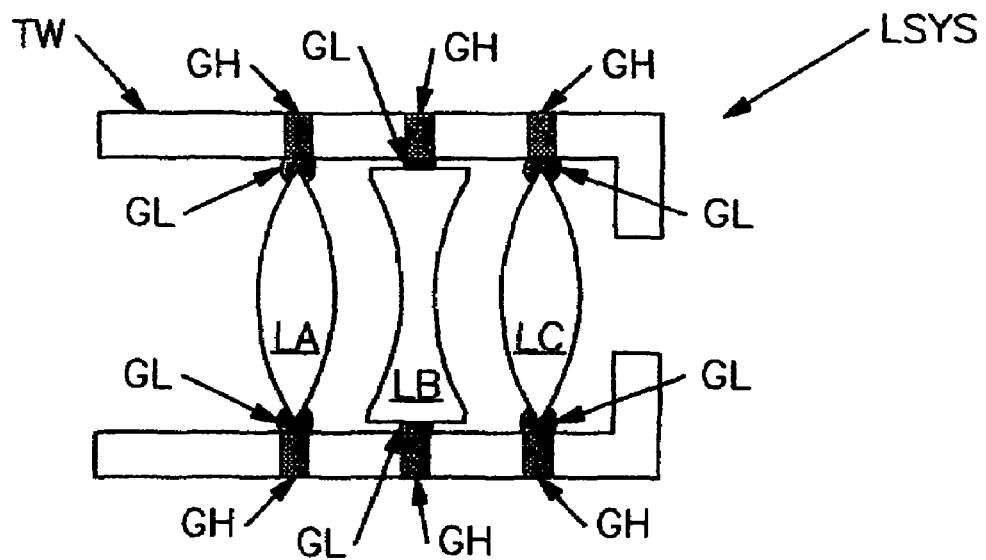
FIG. 2a shows a present invention three element lens, in which the three lenses are secured into a tube by cement applied through holes in the tube wall.
Figure 2B:
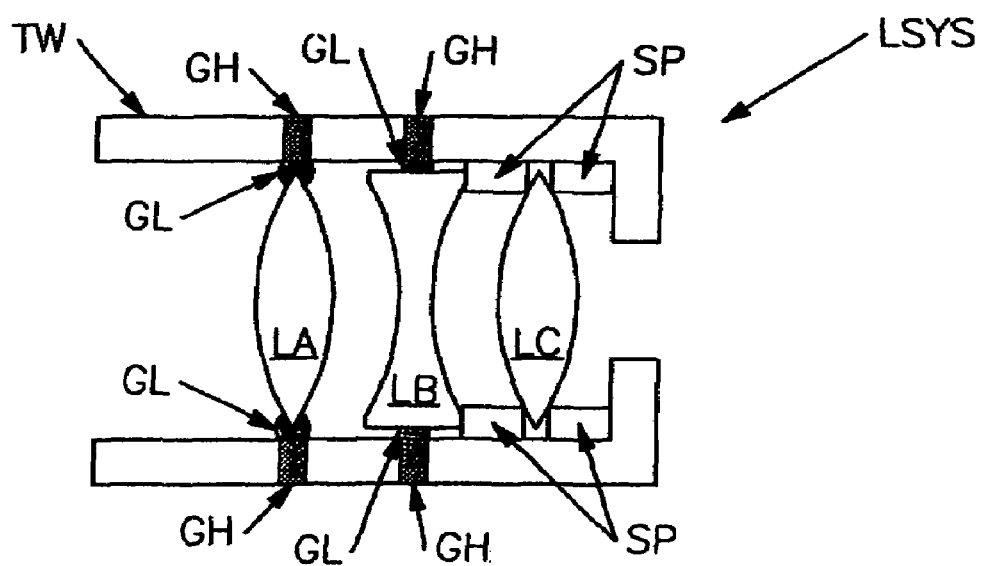
FIG. 2b shows a present invention three element lens system, in which the one lens is secured into a tube by cement applied through holes in the tube wall and two lenses are secured in said tube by stress reducing spacer means.
Figure 2C:
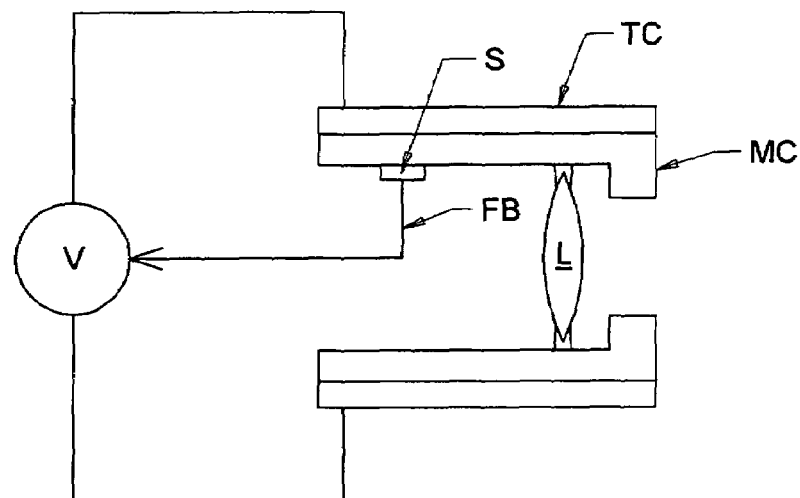
FIG. 2c shows a lens system can provide a lens element in a mounting tube and that a sensor can be present to provide a feedback control signal to a voltage supply that powers a temperature control element.
Figure 2D:
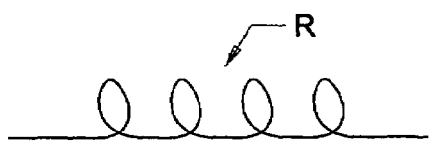
FIG. 2d shows a temperature control element can be a ohmic resistor for heating.
Figure 2E:
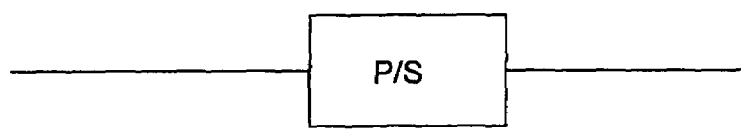
FIG. 2e shows that a temperature control element can be a Peltier or Seebeck unit for cooling.
Figure 2F:
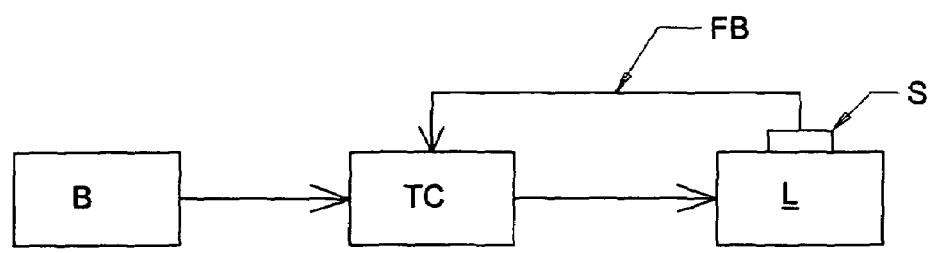
FIG. 2f shows that a blower can be positioned to direct air flow over a heating or cooling element onto a lens element.

(Converging(C))(Diverging(D))(Diverging (D))(Converging(C)); and (Diverging(D))(Converging(C))(Diverging (D))(Converging(C));

And, of course, other configurations within the scope of the present invention include:

(Converging(C))(Diverging(D))(Converging(C)), (see FIGS. 2a and 2b);
(Converging(C))(Converging(C))(Diverging(D));
(Diverging(D))(Diverging(D))(Converging(C));
(Converging(C))(Diverging(D))(Diverging(D));
(Diverging(D))(Converging(C))(Diverging(D));
(Converging(C))(Converging(C))(Diverging(D)) (Diverging( ); and
(Diverging(D))(Diverging(D))(Converging (C))(Converging(C)).

It should be appreciated that the additional elements in d. can then comprise selection(s) from the group consisting of:
beam directing means, (see (PRI) (PRO) in FIG. 1a2);
input lens(es); and
window(s), as in a vacuum chamber;

and the additional elements in f. can then comprise selection(s) from the group consisting of:
beam directing means, (see (PRI) (PRO) in FIG. 1a2);
output lens(es); and
window(s), as in a vacuum chamber.

As described with respect to FIG. 1a3, at least one of the input and output lenses, (generally represented by (AC1) and (AC2) in FIG. 1a1), can, when selected and present, be of multi-element (FE1) (FE3) construction, wherein, for each of said input and output lenses (AC1) and (AC2), when selected and present, at least two elements (FE1) and (FE3) thereof are made from different materials, such that in use the focal length for each wavelength in a range of wavelengths is essentially the same as that for every other wavelength, wherein at least one of said input and output lenses, when selected and present, demonstrates properties selected from the group consisting of:
both demonstrating birefringence;
neither demonstrating birefringence;
one demonstrating birefringence and the other not.

Representative materials from which different elements in said input and output lenses can be made made are calcium fluoride (FE1) (FE1a) (FE1b), and fused silica (FE3), (FE3a) (FE3b).

Another embodiment of an ellipsometer system to which the present invention can be applied to further achieve smaller electromagnetic beam "Spot" size, is shown in FIG. 1a2. FIG. 1a2 shows a Perspective view of a demonstrative system. FIG. 1a2 shows a Light Source (LS) and a Polarizer (P), which in combination serve to produce a generally horizontally oriented Polarized Beam of Electromagnetic Radiation (LBI). Said generally horizontally oriented Polarized Beam of Electromagnetic Radiation (LBI) is caused to interact with Optical Element, (eg. Prism), (PRI), essentially totally internally reflect therein, pass through Focusing Optic (F1) and become generally vertically oriented Polarized Beam of Electromagnetic Radiation (LBI'), then interact with a Material System (MS) present on a Material System supporting Stage (STG). FIG. 1a2 shows that said interaction with the Surface (S) of said Material System (MS) causes a generally vertically oriented Polarized Beam of Electromagnetic Radiation (LBO') to pass through Focusing Optic (F2). FIG. 1a2 shows that after passing through Focusing Optic (F2) said generally vertically oriented Polarized Beam of Electromagnetic Radiation (LBO') interacts with Optical Element, (eg. Prism), (PRO) and is essentially totally internally reflected thereby to become generally horizontally oriented Polarized Beam of Electromagnetic Radiation (LBO), which generally horizontally oriented Polarized Beam of Electromagnetic Radiation (LBO) passes through Analyzer (A) and then enters Detector System (DET), via Circular Aperture (AP), for analysis. It is noted that the purpose of the Focusing Optics (F1) is to produce a very Concentrated High Intensity Small Area Polarized Beam of Electromagnetic Radiation (LBI') from Collimated Polarized Beam of Electromagnetic Radiation (LBI). The purpose of Focusing Optic (F2) is to "Re-Collimate" the generally vertically oriented Polarized Beam of Electromagnetic Radiation (LBO') which results from the Focused Polarized Beam of Electromagnetic Radiation (LBI') being Reflected from said Material System (MS). The Re-Collimated generally vertically oriented Beam of Electromagnetic Radiation (LBI') being identified as generally horizontally oriented Beam of Electromagnetic Radiation (LBO) after it has been caused to interact with Prism (PRO).

FIGS. 1b1-1b4 show, respectively, a positive miniscus lens; a negative miniscus lens; an aspheric convex lens and an aspheric concave lens. Said lens types can be utilized in the present invention at AC1 and/or AC2 and/or AC2' in FIG. 1a1; and at F1 and/or F2 in FIG. 1a2 in addition to or instead of lens configurations shown in FIGS. 1a3, 1a4 and 1a7-1a24.

FIG. 1c shows a more detailed, Top View, of a present invention Detector (DET) system as indicated in FIG. 1a2.

It is noted that (PRI) and (PRO) can be made of the same material, but the preferred embodiment provides that (PRI) be made of BK7 (refractive index approximately 1.55) and that (PRO) be made of F2 (refractive index approximately 1.7).

As regards the present invention, whether provided by a FIG. 1a1 or FIG. 1a2 ellipsometer system configuration, different wavelengths in said Beam which pass through the Focusing Optics (AC1) (F1) can have different focal points, and the resulting "Spectral Spread" can lead to an increased "Spot" size, thereby making it impossible to simultaneously, spectroscopically, investigate a small area on the substrate. An ideal situation therefore is achieved where the Focusing Optics (AC1) (F1) is achromatic, as provided by multi-element lenses such as shown in FIG. 1a3, where element (FE1) is made of a different material than is element (FE3) and where (FE2) is an air gap or equivalent. Such lenses can provide focal lengths which do not significantly change with wavelength, hence provide reduced "Spot" size. Lenses without radial symmetry can also effect change.

It is further noted that FIGS. 1a5 and 1a6 show plots of Spot Size and of Focal Length respectively, verses Wavelength for a Dual Quasi-Achromatic Multi-Element Lens as demonstrated in FIG. 1a4, (which can be considered as present at AC1 or AC2 in FIG. 1a1 and at F1 and/or F2 in FIG. 1a2). Shown also are curves of "Spot Size" and of "Focal Length" verses Wavelength for Fused Silica alone and for Calcium Fluoride ($CaF_2$) alone, and for a lens as shown in FIG. 1a4 where element (FE3) is Fused Silica and element (FE1) is Calcium Fluoride ($CaF_2$). Note the relatively more constant result for a multi-element lens as shown in FIG. 1a4 as compared to the results for single element lenses made from Fused Silica (FE3) and for Calcium Fluoride (FE1).

It is generally presented that achromatic lens systems, as demonstrated in FIGS. 1a3 and 1a4, are usually achieved by combination of two or more singlet lenses, said combination being designed to lessen lens "chromatic aberation", (eg. observable as varying focal length, and/or spot size at a given distance from a lens as a function of wavelength). The source of chromatic characteristics in lenses is found in dispersion by materials from which lenses are made, said dispersion being quantified as a wavelength dependent "index of refraction" which causes different wavelengths of electromagnetic radiation to be refracted differently. Generally, what is required to form achromatic lenses is a combination of two elements which each demonstrate different, (not merely offset), indicies of refraction vs. wavelength curves. When lenses are applied in ellipsometers, chromatic aberation can be detrimental to their performance because it increases spot size of a beam of electromagnetic radiation at the surface of a sample under investigation, which increased spot size is accompanied by spectroscopically varying angle-of-incidence spread, and intensity over the area of said spot. Of course, the larger the spectral range, the more pronounced become the potentially adverse affects of chromatic aberation.

Continuing, for general insight, a shortcoming of Rotating Element Ellipsometer Systems, (other than Rotating Compensator Ellipsometers), generally is that certain Magnitudes of well known Material System characterizing PSI or DELTA can not be monitored thereby. For instance, in Rotating Analyzer Ellipsometer Systems, Material Systems with DELTA near zero (0.0) or one-hundred-eighty (180) Degrees can not be measured. It is also noted that Thin Dielectric Films, such as Nitride and Oxide on semiconductor substrates, often present with a DELTA of one-hundred-eighty (180) Degrees at Angle of Incidence of less than the Brewster Angle, (eg. sixty-five (65) Degrees). The ellipsometer system shown in FIG. 1$a2$ recognizes this problem and can utilize first and/or second Optical Elements, (eg. Prisms), (PRI) and (PRO) which effect Phase Angle Retardation between "P" and "S" Orthogonal Components of a Polarized Beam of Electromagnetic Radiation caused to pass therethrough. (Note that a "P" Component of a Polarized Beam of Electromagnetic Radiation is that Component found to be in a Plane containing both an Incident Beam of Electromagnetic Radiation and a Normal to a Material System Surface, while an "S" Component is that Component perpendicular to said "P" Plane and Parallel to the Material System Surface). The Phase Angle Retardation between X "P" and "S" Orthogonal Components of a Polarized Beam of Electromagnetic Radiation caused to pass therethrough can be caused to Nominally Forty-Five (45) Degrees for each Optical Element (PRI) and (PRO) shown in FIG. 1$a2$, for a total of a Nominal Ninety (90) Degrees. This added Retardation between "P" and "S" Orthogonal Components serves to shift the Material System DELTA's which a Rotating Analyzer Ellipsometer will be unable to measure to Ninety (90) and Two-Hundred-Seventy (270) Degrees. Again, most Thin Film Material Systems present a DELTA of near zero (0.0) and one-hundred-eighty (180) Degrees, hence the first and second Optical Elements (PRI) and (PRO) serve not only to direct a Polarized Beam of Electromagnetic Radiation as desired, but also serve to "Condition" said Polarized Beam of Electromagnetic Radiation so that it can be utilized to measure Material System DELTA's which are in the range of near zero (0.0) Degrees or near one-hundred-eighty (180) degrees.

FIG. 2$a$ demonstrates a present invention Lens System (LSYS) with Three Element (A) (B) and (C), (eg. Three (3) Lenses System), in which the three lenses are secured into a Tube (T) by Cement (GL) applied through Holes (H) in the Tube Wall (TW). It is noted the FIG. 2$a$ approach to mounting multiple lenses is not focused on minimizing birefringence caused by stress, but rather on enabling precise. relative positioning of lenses, and fixing them in place. No mounting system can provide an absolutely stress free mounting of multiple lenses, and it is accurate to state that all practical lenses demonstrate some level of birefringence, and any mounting means can enter stress to a lens. In that sense, the mounting system is not stress-minimizing. FIG. 2$b$ shows a present invention Three (3) Element Lens System (LSYS), in which the lenses (LA) and (LB) are secured into a Tube by Cement (GL) applied through Holes (GH) in the Tube Wall (TW), and Lens (LC) is secured in position in said Tube by Stress Reducing Means comprising Spacers (SP). It is again emphasized that the approach to mounting the Lenses (LA) (LB) and (LC) demonstrated is not Stress Minimizing, but can be described as Stress Reducing. Of course a modification of this system might provide that Lenses (LA) and (LC) be cemented in place, with only Lens (LB) secured in place by Spacers (SP). And additional Lenses, (ie. Lense Elements), can also be present. The distinguishing factor is that at least one Lens present in the Tube is secured in place via Cement (GL) entered via Holes (GH) through the Tube Wall.

FIG. 2$c$ shows a lens system can provide a Lens Element (L) in a mounting tube (MC) and that a sensor (S) can be present to provide a Feedback Control (FB) signal to a Power supply (V) that powers a Temperature Control Element (TC).

FIG. 2$d$ shows a Temperature Control (TC) element can be a Ohmic Resistor (R) for heating.

FIG. 2$e$ shows that a Temperature Control (TC0 element can be a Peltier or Seebeck (P/S) unit for cooling.

FIG. 2$f$ shows that a Blower (B) can be positioned to direct air flow over a Heating or Cooling Temperature Control (TC) element onto a lens (L). Also shown are a Temperature Sensor (S) and a Feedback circuit (FB).

It is to be understood that, for the purposes of this Specification (AC2) and (AC2') in FIG. 1$a_1$, and (F2) in FIG. 1$a_2$ can be considered to be "Phantom Lenses" as originally disclosed in Parent application Ser. No. 09/419,794 Filed Oct. 18, 1999, (now U.S. Pat. No. 6,549,282). In Col. 13, Lines 34-37 of said 282 patent, it is stated that in a two (input-output) lens system in an ellipsometer system, one lens which does not demonstrate birefringence can be a "phantom" lens which is essentially just the atmosphere surrounding a sample system. That is, in effect, only Lens (AC1) in FIG. 1$a_1$, and (F1) in FIG. 1$a_2$.

In summary, multi-element lenses can be produced that provide essentially constant focal lengths and small spot size over a large spectroscopic range of wavelengths, and that said multi-element lenses can be produced which demonstrate small birefringence, and the present invention teaches that control of temperature of at least one lens element cna improve the lens characteistics.

It is emphasized that a system of spatially separated input and output lenses can provide that at least one lens which is not significantly birefringent is selected from the group consisting of: (essentially a surrounding ambient; and a multi-element lens). That is, it is within the scope of the present invention to interpret simple ambient atmosphere as being an input or output lens, and where Claims recite the providing of separated input and output lenses, it should be kept in mind that one of said input and output "lenses" can be effectively the effective absence of any per se. lens. In that light it is emphasized that a present invention ellipsometer system can include a focusing input lens but not an output lens and be an acceptable present invention configuration. That is, while the foregoing disclosure often alludes to the presence of both input and output lenses, said language is to be interpreted generally to include cases wherein only one of said lenses is present, and the other lens is but ambient atmosphere.

It is to be understood that the foregoing presented numerous specific examples of lenses and systems which are non-limiting. For instance, where Claims do not recite specific lens construction, any functional lens construction is to be considered within the scope thereof. That is, while FIGS. 1$a3$, 1$a4$ and 1$a7$-1$a28$ show lens constructions which are preferred, said specific examples are not to be interpreted as limiting in, for instance, Method Claims for accurately evaluating parameters in parameterized equations in a mathematical model of a system of spatially separated input and output optical elements. Claims which do not recite specific lens construction are not to be read as limited by specific examples shown, where functional equivalents can be successfully applied. For instance, it is specifically noted that either void region, FE2a or FE2b, in FIG. 1a4 can be absent, as where elements FE1a and FE3a make direct contact over their mid-region, and/or where FE1b and FE3b make direct contact over their mid-region thereof. This can occur, for instance, where the convex curvature of lens element FE1a is the same as the concave curvature of element FE3a in FIG. 1a3. Additionally, while preferred lenses applied in the present invention, as shown in FIG. 1a3, comprise two elements, where specific lens construction is not recited in a Claim, it is to be understood that any number of, and type of, elements can comprise a lens, (eg. comprise more than two elements, comprise meniscus and/or aspheric elements with radial or non-radial symmetry).

It is further specifically noted that while the lenses shown in FIGS. $1a_3$, $1a_4$ and $1a_7$-$1a_{28}$ are typically selected to demonstrate radial symmetry, it is within the scope of the present invention to utilize non-radially symmetric lenses, where, for instance, a spot size length to width aspect ratio is to be modified thereby. Therefore any lens shown or indicated in FIGS. $1a_3$, $1a_4$ and $1a_7$-$1a_{28}$ can be designed to demonstrate radial symmetry, or non-radial symmetry, or be of any other functional type, where the achromatic properties are present. And, it is to be understood that FIGS. $1a_3$, $1a_4$, $1a_7$-$1a_{28}$ and $2a$ and $2b$ are to be interpreted in the sense of the terminology "comprising". That is, while, for instance, FIG. $1a_7$ show two elements, it can be interpreted to be a two element lens per se., or to be part of a three or more element lens. As an example, FIG. $1a_7$ shows two lenses of the three lens system of FIGS. $2a$ and $2b$.

It is also to be understood that terminology such as "multi-element lenses" and the terminology "multiple lenses" system are used interchangeably in this Specification. That is, a lens system can be considered to be comprised of multiple elements or of multiple lenses and refer to the same system.

It is further to be understood that while cement entered through holes in a tube wall has been used as an exemplary preferred primary present invention means of securing a lens, or lens element(s) in place after appropriate positioning, it is within the scope of the present invention to firmly secure a lens or lens element(s) to the inner wall of a tube by securing means other than cement, with said "other securing means" being interpreted sufficiently broadly to include crimping or set-screws and other functional equivalents.

It is also specifically stated that it is believed that where at least one of at least two lenses in a multi-lens, (or elements in a multi-element lens system), is mounted in other than a manner specifically designed for—minimizing stress—thereon in order to minimize stress induced birefringence in said system, particularly where the lenses or lens elements are glued into a tubular system, then said lens system, in the context of application in an ellipsometer or polarimeter, is Patentable.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer or polarimeter system comprising at least one multi-element lens placed at a selection from the group consisting of:
   at the input; and
   at the output;
   said at least one multi-element lens being comprised of at least two elements which are made of different materials, such that in use the focal length for each wavelength in a range of wavelengths is essentially the same for every other wavelength in said range of wavelengths, wherein said multi-element lens demonstrates at least some birefringence;
   said multi-element lens being part of a system for controlling the temperature of said multi-element lens.

2. An ellipsometer or polarimeter system comprising at least one multi-element lens as in claim 1, in which the sequence of lenses is characterized by a selection for the group:
   (Converging(C))(Diverging(D))(Converging(C));
   (Converging(C))(Converging(C))(Diverging(D));
   (Diverging(D))(Diverging(D))(Converging(C));
   (Converging(C))(Diverging(D))(Diverging(D));
   (Diverging(D)) (Converging(C))(Diverging(D));
   (Converging(C))(Converging(C))(Diverging(D)) (Diverging(D));
   (Diverging(D))(Diverging(D))(Converging(C)) (Converging(C));
   ((Diverging(D))(Converging(C))(Converging(C)) (Diverging(D));
   (Converging(C))(Diverging(D))(Converging (C))(Diverging(D));
   (Converging(C))(Diverging(D))(Diverging (D))(Converging(C)); and
   (Diverging(D))(Converging(C))(Diverging (D))(Converging(C)).

3. An ellipsometer or polarimeter as in claim 1, in which the at least one multi-element lens is sequentially comprised of three elements:
   Calcium Fluoride;
   Fused Silica;
   Calcium Fluoride;
   said Calcium Fluoride-Fused Silica-Calcium Fluoride elements being cemented into a mounting system which comprises a tube with holes through the wall thereof through which cement is entered to secure said three elements, such that at least one of said lens elements is mounted in other than a manner specifically designed for minimizing stress thereon to minimize stress induced birefringence in said multi-element lens.

4. An ellipsometer or polarimeter as in claim 1, in which the at least one multi-element lens is sequentially comprised of first and second elements which are each independently selected from the group consisting of:
   $CaF_2$;
   $BaF_2$;
   LiF; and
   $MgF_2$;
   fused silica;
   a void region;
   a gas filled region;
   a liquid filled region; and
   a functional equivalent to a void region;
   said elements being cemented into a mounting system which comprises a tube with holes through the wall thereof through which cement is entered to secure said at least first and second elements, such that at least one of said lens elements is mounted in other than a manner specifically designed for minimizing stress thereon to minimize stress induced birefringence in said multi-element lens.

5. An ellipsometer or polarimeter as in claim 1, which further comprises a broadband source for generating a polychromatic probe beam and a polarizer prior to a sample; and an analyzer and detector after said sample.

6. An ellipsometer or polarimeter as in claim 1, which further comprises a broadband source for generating a polychromatic probe beam and a polarizer prior to a sample; and an analyzer and detector after said sample, said ellipsometer or polarimeter further having at least one compensator present at least one location selected from the group consisting of:
   before said sample; and
   after said sample.

7. An ellipsometer or polarimeter system comprising at least one multi-element lens placed at a selection from the group consisting of:
   at the input; and
   at the output;
said at least one multi-element lens being comprised of at least two elements which are made of different materials, such that in use the focal length for each wavelength in a range of wavelengths is essentially the same for every other wavelength in said range of wavelengths, at least one of said elements being cemented into a tube which comprises at least one hole through the wall thereof for entering said cement; said ellipsometer or polarimeter system further comprising a broadband source for generating a polychromatic probe beam and a polarizer prior to a sample, and an analyzer and detector after said sample; and said polarimeter or ellipsometer further having at least one compensator present at least one location selected from the group consisting of:
   before said sample; and
   after said sample;
said ellipsometer or polarimeter being characterized by the presence of a temperature control system which is positioned to control the temperature of at least one lens element.

8. A broadband ellipsometer or polarimeter for evaluating the characteristics of a sample comprising:
   a broadband light source for generating a polychromatic probe beam, said polychromatic probe beam comprising at least UV and Visible wavelengths; an all refractive optical focusing system for focusing the probe beam onto a spot on the surface of the sample, said all-refractive focusing optical system comprising at least two lenses that are substantially transparent to UV, visible or NIR wavelengths, two of said at least two lenses being made of calcium fluoride and fused silica, said lenses being present in a tube which comprises at least one hole through the wall thereof for accepting cement;
such that at least a first said lens is placed in said tube at the location of a hole for accepting cement and cement is entered thereinto and allowed to dry, thereby securing said lens in place in said tube; and such that an additional lens is mounted in said tube by a selection from the group consisting of:
   being similarly cemented into place in said tube at a precise location with respect to said first lens; and
   being positioned in said tube with respect to said first lens in a stress reducing manner comprising spacer means for maintaining relative position between said lenses;
said broadband ellipsometer or polarimeter system further comprising an analyzer system for monitoring at least a portion of a probe beam reflected from said sample and generating output signals responsive thereto, and a processor for evaluating characteristics of the sample based on said output signals;
said broadband ellipsometer or polarimeter being further characterized by the presence of a temperature control system located to control the temperature of at least one lens element.

9. A broadband ellipsometer as in claim 8 in which there are three lenses present in said tube, each thereof being located with respect to holes through the wall of said tube and secured in said position by cement which is entered into said holes.

10. A broadband ellipsometer as in claim 9 in which the three lenses are two calcium fluoride lenses disposed on opposite sides of a fused silica lens.

11. A broadband ellipsometer as in claim 8, in which at least one of said at least two lenses is mounted in other than a manner specifically designed for minimizing stress thereon to minimize stress induced birefringence in said multi-element lens.

12. A broadband ellipsometer as in claim 9, in which at least one of/said at least two lenses is mounted in other than a manner specifically designed for minimizing stress thereon to minimize stress induced birefringence in said at least one lens.

13. A broadband ellipsometer as in claim 8, in which the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved, and wherein cement is entered through holes in the wall of said tube which are near edges of said at least two lenses, to secure the positions of said lenses.

14. A method of improving the operation of a broadband ellipsometer or polarimeter for evaluating the characteristics of a sample comprising:
   a) providing broadband ellipsometer or polarimeter which comprises:
      broadband light source means for generating a polychromatic probe beam, said polychromatic probe beam comprising at least UV and Visible wavelengths;
      an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium fluoride and fused silica, said lenses being present in a tube which comprises holes through the wall thereof for accepting cement,
   said broadband ellipsometer or polarimeter being characterized by the presence of a temperature control system positioned to control the temperature of at least one lens element;
   b) effecting the relative position between at least two of said at least two lenses in said tube by, while actively monitoring of the effect of said at least two lenses on a beam of electromagnetic radiation caused to pass therethrough, adjusting said relative position until an acceptable effect is achieved on said electromagnetic beam, and wherein cement is entered through holes in the wall of said tube which are near edges of said at least two lenses, to secure the positions of said lenses;
   such that said at least two lenses are precisely secured in said tube at desired locations relative to one another;
   c) causing said temperature control system to effect a desired lens element temperature.

15. A method as in claim 14, in which there are three lenses present in said tube, each thereof being precisely located with respect to one another and secured in said position by cement which is entered into said holes through the wall of said tube when an acceptable effect on said beam of electromagnetic radiation is achieved.

16. A method as in claim 15, in which the three lenses which are precisely positioned with respect to one another are two calcium fluoride lenses disposed on opposite sides of a fused silica lens.

17. A broadband ellipsometer or polarimeter for evaluating the characteristics of a sample comprising:
 a broadband light source for generating a polychromatic probe beam, said polychromatic probe beam comprising at least UV and Visible wavelengths, an all refractive optical focusing system for focusing the probe beam onto a spot on the surface of the sample, said all-refractive focusing optical system comprising at least two lenses that are substantially transparent to UV and visible wavelengths, two of said at least two lenses being made of calcium fluoride and fused silica, said lenses being present in a tube which comprises holes through the wall thereof for accepting cement;
such that lenses are placed in said tube at the location of said holes for accepting cement and cement is entered thereinto and allowed to dry, thereby securing said lenses in place;
said broadband ellipsometer or polarimeter system further comprising a temperature control system positioned to control the temperature of at least one lens element;
said broadband ellipsometer or polarimeter system further comprising an analyzer system for monitoring a portion of a probe beam reflected from said sample and generating output signals responsive thereto, and a processor for evaluating characteristics of the sample based on the output signals;
said broadband ellipsometer or polarimeter being distinguished in that the relative position between at least two of said at least two lenses in said tube is precisely controlled by, while actively monitoring of the effect of said at least two lenses on a beam of electromagnetic radiation caused to pass therethrough, adjusting said relative position until an acceptable effect is achieved on said beam of electromagnetic radiation, and wherein cement is entered through holes in the wall of said tube which are near edges of said at least two lenses, to secure the positions of said lenses.

18. A broadband ellipsometer or polarimeter as in claim 17, in which there are three lenses present and in which the relative position between the first and second, and/or between the second and third is precisely controlled prior to cementing them into position in said tube.

19. A broadband ellipsometer or polarimeter as in claim 17, in which the temperature control system comprises means for effecting at least one selection from the group consisting of:
 heating; and
 cooling.

20. A broadband ellipsometer or polarimeter as in claim 19, in which the temperature control system further comprises a sensor for sensing the temperature of at least one lens element, and feedback means.

21. A broadband ellipsometer or polarimeter as in claim 17, in which the sequence of lenses is characterized by a selection for the group:
 (Converging(C))(Diverging(D))(Converging(C));
 (Converging(C))(Converging(C))(Diverging(D));
 (Diverging(D))(Diverging(D))(Converging(C));
 (Converging(C))(Diverging(D))(Diverging(D));
 (Diverging(D))(Converging(C))(Diverging(D));
 (Converging(C))(Converging(C))(Diverging(D))(Diverging(D));
 (Diverging(D))(Diverging(D))(Converging(C))(Converging(C));
 ((Diverging(D))(Converging(C))(Converging(C))(Diverging(D));
 (Converging(C))(Diverging(D))(Converging(C))(Diverging(D));
 (Converging(C))(Diverging(D))(Diverging(D))(Converging(C)); and
 (Diverging(D))(Converging(C))(Diverging(D))(Converging(C)).

22. A broadband ellipsometer or polarimeter as in claim 17, in which the sequence of lens elements is sequentially comprised of at least first and second elements which are each independently selected from the group consisting of:
 $CaF_2$;
 $BaF_2$;
 LiF; and
 $MgF_2$
 fused silica;
 a void region;
 a gas filled region;
 a liquid filled region;
 a functional equivalent to a void region.

23. An ellipsometer or polarimeter system comprising at least one multi-element lens placed at a selection from the group consisting of:
 at the input; and
 at the output;
said at least one multi-element lens being comprised of at least two elements which are made of different materials, such that in use the focal length for each wavelength in a range of wavelengths is essentially the same for every other wavelength in said range of wavelengths, at least one of said elements being firmly secured to the inner wall of a tube by securing means;
said ellipsometer or polarimeter system further comprising a temperature control system positioned to control the temperature of at least one lens element of said at least one multi-element lens;
said ellipsometer or polarimeter system further comprising a broadband source for generating a polychromatic probe beam and a polarizer prior to a sample, and an analyzer and detector after said sample; and said polarimeter further having at least one compensator present at least one location selected from the group consisting of:
 before said sample; and
 after said sample.

24. A broadband ellipsometer or polarimeter as in claim 23, in which the sequence of lenses is characterized by a selection for the group:
 (Converging(C))(Diverging(D))(Converging(C));
 (Converging(C))(Converging(C))(Diverging(D));
 (Diverging(D))(Diverging(D))(Converging(C));
 (Converging(C))(Diverging(D))(Diverging(D));
 (Diverging(D))(Converging(C))(Diverging(D));
 (Converging(C))(Converging(C))(Diverging(D))(Diverging(D));
 (Diverging(D))(Diverging(D))(Converging(C))(Converging(C));
 (Diverging(D))(Converging(C))(Converging(C))(Diverging(D));
 (Converging(C))(Diverging(D))(Converging(C)) (Diverging(D));
 (Converging(C)) (Diverging(D)) (Diverging(D))(Converging(C)); and
 (Diverging(D)) (Converging(C))(Diverging(D))(Converging(C)).

25. A broadband ellipsometer or polarimeter as in claim 23, in which there are three lenses having a combined focal length (F), the first lens being a positive lens made from a first material, the second lens being a negative lens made from a second material, and the third lens being a positive lens made from a third material, said three lenses having "n" faces numbered 1-6, with "rn" being the radius of curvature of the nth face, and "tn" being the spacing nth and (n+1)st face;

at least one of said "r2" and/or "t4" being other than:

r2<F;

t4>0.05F;

and at least one of said "r4" and/or "r5" optionally being other than:

r4>2.5F r5>0.5F.

26. A lens system comprising a lens and a mounting means for securing said lens, said lens system further comprising means for controlling the temperature of said lens system; said lens system being present in an ellipsometer or polarimeter system comprising:
- a source of electromagnetic radiation;
- a polarizer;
- a sample;
- an analyzer; and
- a detector of electromagnetic radiation;
- wherein said lens system is positioned at a selection from the group consisting of:
  - between said source of electromagnetic radiation and said sample; and
  - between said sample and said detector of electromagnetic radiation.

27. A lens system as in claim 26 in which means for controlling the temperature of said lens provides heating capability.

28. A lens system as in claim 26 in which means for controlling the temperature of said lens provides cooling capability.

29. A lens system as in claim 28 in which means for controlling the temperature of said lens comprises a Peltier system.

30. A lens system as in claim 28 in which means for controlling the temperature of said lens comprises a resistance heating element.

31. A lens system as in claim 26 in which means for controlling the temperature of said lens includes temperature sensing means for sensing the temperature of the lens.

32. A lens system as in claim 31 in which means for controlling the temperature of said lens comprises a feedback circuit which provides output from said temperature sensing means to a means for controlling the temperature of said lens selected from the group consisting:
- means for cooling said lens; and
- means for heating said lens.

33. A lens system as in claim 32 in which the means for controlling the temperature of said lens comprises a feedback circuit which operates to compensate changes in lens temperature.

34. A lens system as in claim 26 in which said lens system is characterized by at least one selection form the group consisting of:
- said lens has at least two elements;
- said lens comprises at least one element made of CaF2; and
- the mounting means for securing said lens is made of aluminum.

35. A lens system as in claim 27 in which said lens system is characterized by at least one selection form the group consisting of:
- said lens has at least two elements;
- said lens comprises at least one element made of CaF2; and
- the mounting means for securing said lens is made of aluminum.

36. A lens system as in claim 28 in which said lens system is characterized by at least one selection form the group consisting of:
- said lens has at least two elements;
- said lens comprises at least one element made of CaF2; and
- the mounting means for securing said lens is made of aluminum.

37. A lens system as in claim 29 in which said lens system is characterized by at least one selection form the group consisting of:
- said lens has at least two elements;
- said lens comprises at least one element made of CaF2; and
- the mounting means for securing said lens is made of aluminum.

38. A lens system as in claim 30 in which said lens system is characterized by at least one selection form the group consisting of:
- said lens has at least two elements;
- said lens comprises at least one element made of CaF2; and
- the mounting means for securing said lens is made of aluminum.

39. A lens system as in claim 31 in which said lens system is characterized by at least one selection form the group consisting of:
- said lens has at least two elements;
- said lens comprises at least one element made of CaF2; and
- the mounting means for securing said lens is made of aluminum.

40. A lens system as in claim 32 in which said lens system is characterized by at least one selection form the group consisting of:
- said lens has at least two elements;
- said lens comprises at least one element made of CaF2; and
- the mounting means for securing said lens is made of aluminum.

41. A lens system as in claim 33 in which said lens system is characterized by at least one selection form the group consisting of:
- said lens has at least two elements;
- said lens comprises at least one element made of CaF2; and
- the mounting means for securing said lens is made of aluminum.

* * * * *